(12) United States Patent
Vela Hernández et al.

(10) Patent No.: US 9,782,483 B2
(45) Date of Patent: Oct. 10, 2017

(54) SIGMA LIGANDS FOR THE PREVENTION AND/OR TREATMENT OF EMESIS INDUCED BY CHEMOTHERAPY OR RADIOTHERAPY

(75) Inventors: José Miguel Vela Hernández, Barcelona (ES); Xavier Codony-Soler, Mataró-Barcelona (ES); Daniel Zamanillo-Castanedo, Barcelona (ES)

(73) Assignee: Laboratories Del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 13/698,718

(22) PCT Filed: May 20, 2011

(86) PCT No.: PCT/EP2011/058224
§ 371 (c)(1),
(2), (4) Date: Jan. 15, 2013

(87) PCT Pub. No.: WO2011/144721
PCT Pub. Date: Nov. 24, 2011

(65) Prior Publication Data
US 2013/0109692 A1    May 2, 2013

(30) Foreign Application Priority Data
May 21, 2010 (EP) .................... 10382136

(51) Int. Cl.
| | | |
|---|---|---|
| A61K 45/06 | (2006.01) |
| C07D 231/22 | (2006.01) |
| A61K 31/5377 | (2006.01) |
| A61K 31/337 | (2006.01) |
| A61K 31/4523 | (2006.01) |
| A61K 31/4725 | (2006.01) |
| A61K 31/475 | (2006.01) |
| A61K 31/496 | (2006.01) |
| A61K 33/24 | (2006.01) |

(52) U.S. Cl.
CPC ............ *A61K 45/06* (2013.01); *A61K 31/337* (2013.01); *A61K 31/4523* (2013.01); *A61K 31/475* (2013.01); *A61K 31/4725* (2013.01); *A61K 31/496* (2013.01); *A61K 31/5377* (2013.01); *A61K 33/24* (2013.01); *C07D 231/22* (2013.01)

(58) Field of Classification Search
None
See application file for complete search history.

(56) References Cited

U.S. PATENT DOCUMENTS

| | | |
|---|---|---|
| 2,908,677 A | 10/1959 | Straley et al. |
| 3,514,439 A | 5/1970 | Wehrli et al. |
| 3,980,675 A | 9/1976 | Venturello et al. |
| 4,024,175 A | 5/1977 | Satzinger et al. |
| 4,207,392 A | 6/1980 | Shiao et al. |
| 4,234,479 A | 11/1980 | Mennicke et al. |
| 4,234,616 A | 11/1980 | Shu et al. |
| 4,337,263 A | 6/1982 | Techer et al. |
| 5,948,777 A | 9/1999 | Bender et al. |
| 6,057,371 A * | 5/2000 | Glennon ............... 514/649 |
| 6,100,259 A | 8/2000 | Xiang et al. |
| 6,166,072 A | 12/2000 | Bell et al. |
| 6,492,529 B1 | 12/2002 | Kapadia et al. |
| 6,509,367 B1 | 1/2003 | Martin et al. |
| 7,091,257 B2 | 8/2006 | Greer, IV |
| 7,105,646 B2 | 9/2006 | Chamberlain et al. |
| 7,696,199 B2 | 4/2010 | Laggner et al. |
| 7,799,782 B2 | 9/2010 | Munson et al. |
| 7,988,966 B2 | 8/2011 | Pavone |
| 8,193,223 B2 | 6/2012 | Jagerovic et al. |
| 8,293,740 B2 | 10/2012 | Laggner et al. |

(Continued)

FOREIGN PATENT DOCUMENTS

| | | |
|---|---|---|
| EP | 0248594 A2 | 12/1987 |
| EP | 0414289 A1 | 2/1991 |

(Continued)

OTHER PUBLICATIONS

Silvey et al. in Journal of Clinical Oncology 6(9), 1397-1400 (1988) (Abstract).*

(Continued)

*Primary Examiner* — Dennis Heyer
(74) *Attorney, Agent, or Firm* — Gary J. Gershik; Cooper & Dunham LLP

(57) ABSTRACT

The invention refers to the use of a sigma ligand, preferably a sigma ligand of formula (I), to prevent or treat emesis induced by a chemotherapeutic agent or radioactivity, especially emesis induced by taxanes, vinca alkaloids or platin chemotherapeutic drugs.

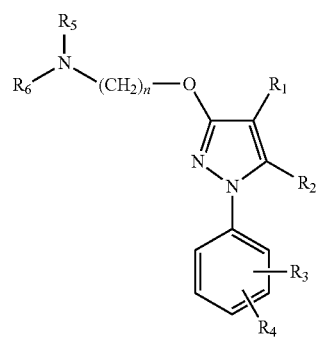

13 Claims, 1 Drawing Sheet

(56) References Cited

U.S. PATENT DOCUMENTS

| | | |
|---|---|---|
| 8,314,096 B2 | 11/2012 | Laggner et al. |
| 8,470,867 B2 | 6/2013 | Laggner et al. |
| 8,492,425 B2 | 7/2013 | Torrens et al. |
| 8,877,753 B2 | 11/2014 | Buschmann |
| 2003/0144309 A1 | 7/2003 | Choon-Moon |
| 2005/0020483 A1 | 1/2005 | Oksenberg |
| 2006/0106068 A1 | 5/2006 | Laggner |
| 2007/0208134 A1 | 9/2007 | Hunter et al. |
| 2008/0058362 A1 | 3/2008 | Singh et al. |
| 2008/0125416 A1* | 5/2008 | Laggner et al. ........... 514/227.8 |
| 2008/0161604 A1 | 7/2008 | Calvani et al. |
| 2009/0018151 A1 | 1/2009 | Fink |
| 2009/0264442 A1 | 10/2009 | Cuberes-Altisent et al. |
| 2009/0325975 A1 | 12/2009 | Buschmann |
| 2010/0081659 A1 | 4/2010 | Laggner |
| 2010/0190078 A1 | 7/2010 | Rapaport et al. |
| 2010/0190780 A1 | 7/2010 | Laggner et al. |
| 2010/0190781 A1 | 7/2010 | Laggner et al. |
| 2010/0240711 A1 | 9/2010 | Takada et al. |
| 2011/0036951 A1 | 2/2011 | Moorer et al. |
| 2011/0112095 A1 | 5/2011 | Buschmann et al. |
| 2011/0269727 A1 | 11/2011 | Toledano |
| 2012/0141606 A1 | 6/2012 | Baeyens-Cabrera et al. |
| 2012/0232093 A1 | 9/2012 | Cuberes-Altisent et al. |
| 2012/0283262 A1 | 11/2012 | Soler Ranzani et al. |
| 2012/0302568 A1 | 11/2012 | Vela Hernandez et al. |
| 2012/0316336 A1 | 12/2012 | Berenguer-Maimo et al. |
| 2013/0109692 A1 | 5/2013 | Vela Hernandez et al. |
| 2013/0143884 A1 | 6/2013 | Cuberes-Altisent et al. |
| 2013/0158033 A1 | 6/2013 | Vela Hernandez et al. |
| 2013/0324535 A1 | 12/2013 | Zamanillo-Castanedo et al. |
| 2015/0018354 A1 | 1/2015 | Buschmann et al. |
| 2016/0220575 A1 | 8/2016 | Baeyens-Cabrera et al. |

FOREIGN PATENT DOCUMENTS

| | | | |
|---|---|---|---|
| EP | 0431943 A2 | 6/1991 | |
| EP | 0445974 A2 | 9/1991 | |
| EP | 0518805 A1 | 12/1992 | |
| EP | 0529973 A1 | 3/1993 | |
| EP | 0 441 333 | 5/1994 | |
| EP | 0975648 A1 | 2/2000 | |
| EP | 1130018 A1 | 9/2001 | |
| EP | 1634872 A1 | 3/2006 | |
| EP | 1634873 A1 | 3/2006 | |
| EP | 1829866 A1 | 9/2007 | |
| EP | 1829875 A1 | 9/2007 | |
| EP | 1847542 A1 | 10/2007 | |
| EP | 1787679 A1 | 11/2008 | |
| EP | 2090311 A1 | 8/2009 | |
| EP | 2112139 A1 | 10/2009 | |
| EP | 2113501 A1 | 11/2009 | |
| EP | 2116539 A1 | 11/2009 | |
| EP | 2353598 A1 | 8/2010 | |
| EP | 2254579 A1 | 12/2010 | |
| EP | 2 292 236 | 3/2011 | |
| EP | 2353591 A1 | 8/2011 | |
| EP | 2361904 A1 | 8/2011 | |
| EP | 2415471 A1 | 2/2012 | |
| EP | 2335688 A1 | 6/2012 | |
| EP | 2460519 A1 | 6/2012 | |
| EP | 2460804 A1 | 6/2012 | |
| EP | 2524694 A1 | 11/2012 | |
| EP | 2395003 A1 | 12/2012 | |
| EP | 2426111 A1 | 3/2013 | |
| EP | 2426112 A1 | 3/2013 | |
| EP | 2792352 A1 | 10/2014 | |
| EP | 2818166 A1 | 12/2014 | |
| EP | 3043795 A1 | 7/2016 | |
| EP | 3082790 A1 | 10/2016 | |
| ES | 2251316 A1 | 10/2004 | |
| ES | WO 2009/103487 * | 8/2009 | ........... A61K 31/495 |
| FR | 2301250 A1 | 9/1976 | |
| FR | 2472564 A1 | 7/1981 | |
| GB | 1088973 A | 10/1967 | |
| GB | 1496411 A | 12/1977 | |
| GB | 2026482 A | 7/1987 | |
| IL | 15153 B | 3/2008 | |
| JP | 1992/364129 | 12/1992 | |
| JP | 10036259 | 2/1998 | |
| JP | 10055048 | 2/1998 | |
| JP | 2004/196678 | 7/2004 | |
| JP | 2008/510767 | 4/2008 | |
| JP | 2008/179541 | 8/2008 | |
| RU | 2218187 C2 | 10/2003 | |
| RU | 2322977 C1 | 4/2008 | |
| RU | 2382646 C1 | 2/2010 | |
| SU | 11248 | 9/1929 | |
| WO | WO-91/09594 A1 | 7/1991 | |
| WO | WO-92/09560 A1 | 6/1992 | |
| WO | WO-93/23383 A1 | 12/1992 | |
| WO | WO-96/16063 A1 | 5/1996 | |
| WO | WO-98/46618 A1 | 10/1998 | |
| WO | WO-99/01444 A1 | 1/1999 | |
| WO | WO-99/21824 A1 | 5/1999 | |
| WO | WO-99/31057 A1 | 6/1999 | |
| WO | WO-99/31074 A2 | 6/1999 | |
| WO | WO-99/31075 A1 | 6/1999 | |
| WO | WO-99/59409 A1 | 11/1999 | |
| WO | WO-99/61424 A1 | 12/1999 | |
| WO | WO-00/31020 A1 | 2/2000 | |
| WO | WO-00/20005 A1 | 4/2000 | |
| WO | WO-00/27394 A1 | 5/2000 | |
| WO | WO-00/40275 A2 | 7/2000 | |
| WO | WO-00/73259 A1 | 12/2000 | |
| WO | WO-00/73296 A2 | 12/2000 | |
| WO | WO-00/73300 A1 | 12/2000 | |
| WO | WO-02/085839 A1 | 10/2002 | |
| WO | WO-02/092573 A2 | 11/2002 | |
| WO | WO-02/102387 A1 | 12/2002 | |
| WO | WO-03/080183 A1 | 10/2003 | |
| WO | WO-2004/016592 A1 | 2/2004 | |
| WO | WO-2004/017961 A2 | 3/2004 | |
| WO | WO-2004/046129 A2 | 6/2004 | |
| WO | WO-2005/061462 A2 | 7/2005 | |
| WO | WO-2006/010587 A1 | 2/2006 | |
| WO | WO 2006/021462 | 3/2006 | |
| WO | WO-2006/021462 A1 | 3/2006 | |
| WO | WO-2006/021463 A1 | 3/2006 | |
| WO | WO-2006/027221 A1 | 3/2006 | |
| WO | WO-2006/118307 A1 | 11/2006 | |
| WO | WO-2007/002559 A1 | 1/2007 | |
| WO | WO-2007/025613 A2 | 3/2007 | |
| WO | WO-2007/046550 A1 | 4/2007 | |
| WO | WO 2007/046650 | 4/2007 | |
| WO | WO-2007/079086 A1 | 7/2007 | |
| WO | WO-2007/090661 A2 | 8/2007 | |
| WO | WO 2007/098939 | 9/2007 | |
| WO | WO-2007/098953 A1 | 9/2007 | |
| WO | WO-2007/098963 A1 | 9/2007 | |
| WO | WO-2007/098964 A2 | 9/2007 | |
| WO | WO-2007/108517 A1 | 9/2007 | |
| WO | WO-2007/110221 A1 | 10/2007 | |
| WO | WO-2007/141018 A1 | 12/2007 | |
| WO | WO-2008/015266 A1 | 2/2008 | |
| WO | WO-2008/055932 A1 | 5/2008 | |
| WO | WO-2008/108517 A2 | 9/2008 | |
| WO | WO 2008/149062 | 12/2008 | |
| WO | WO-2009/038112 A1 | 3/2009 | |
| WO | WO-2009/071657 A1 | 6/2009 | |
| WO | WO 2009/103487 | 8/2009 | |
| WO | WO-2009/103487 A1 | 8/2009 | |
| WO | WO-2009/130310 A1 | 10/2009 | |
| WO | WO-2009/130314 A1 | 10/2009 | |
| WO | WO-2009/130331 A1 | 10/2009 | |
| WO | WO-2011/095579 A1 | 1/2011 | |
| WO | WO-2011/018487 A1 | 2/2011 | |
| WO | WO-2011/064296 A1 | 6/2011 | |
| WO | WO-2011/064315 A1 | 6/2011 | |
| WO | WO-2011/095584 A1 | 8/2011 | |
| WO | WO-2011/095585 A1 | 8/2011 | |
| WO | WO-2011/144721 A1 | 11/2011 | |
| WO | WO-2011/147910 A1 | 12/2011 | |
| WO | WO-2012/016980 A1 | 2/2012 | |

(56) References Cited

FOREIGN PATENT DOCUMENTS

| WO | WO-2012/019984 A1 | 2/2012 |
|---|---|---|
| WO | WO-2012/072781 A1 | 6/2012 |
| WO | WO-2012/072782 A1 | 6/2012 |
| WO | WO-2012/156497 A1 | 11/2012 |
| WO | WO-2012/158413 A2 | 11/2012 |
| WO | WO-2014/170319 A1 | 10/2014 |
| WO | WO-2014/207024 A1 | 12/2014 |
| WO | WO-2015/036470 A1 | 3/2015 |
| WO | WO-2015-091505 A1 | 6/2015 |
| WO | WO-2015/091508 A1 | 6/2015 |

OTHER PUBLICATIONS

Hudzik et al. in European Journal of Pharmacology, 236 (1993) 279-287.*
Owens et al. in Clinical Pharmacy 3(2), 167-170 (1984).*
Gralla et al. in Annals of Internal Medicine 95(4), 414-420 (1981).*
Schetz et al. in Brain Research 1181 (2007) 1-9.*
Van Sickle et al. Gastroenterology 121(4), 767-774 (2001) (Abstract).*
Tyers et al. Oncology 49(4), 263-268 (1992) (Abstract).*
Hudzik et al. in European Journal of Pharmacology 236 1993) 279-287.*
Hayashi et al. in CNS Drugs 18(5), 269-284 (2004).*
Zhang et al. in Synapse 15(4):276-284 (1993), Abstract.*
Paquette et al. in Psychopharmacology (Berlin) 204(4):743-754 (2009).*
Brammer et al. in European Journal of Pharmacology, 553, 141-145 (2006).*
Aapro, M. et al., "Anticipatory Nausea and Vomiting", Support Care Cancer, 2005, vol. 13, pp. 117-121.
Argyriou, A.A. et al., "Bortezomib-Induced Peripheral Neuropathy in multiple Myeloma: a comprehensive review of the literature", Blood, 2008, vol. 112, pp. 1593-1599.
Barnes, J.M. et al., "Reserpine, *Para*-Chlorophenylalanine and Fenfluramine Antagonise Cisplatin-Induced Emesis in the Ferret", Neuropharmacology, 1988, vol. 27, No. 8, pp. 783-790.
Crawford, K.W. and Bowen, W.D., "Sigma-2 Receptor Agonists Activate a Novel Apoptotic Pathway and Potentiate Antineoplastic Drugs in Breast Tumor cell Lines", Cancer Research, 2002, vol. 62, pp. 313-322.
Guitart, X., et al., "Sigma receptors biology and therapeutic potential", Psychophamacology, 2004, vol. 174, pp. 301-319.
Grunberg, S.M., at al., "incidence of Chemotherapy-Induced Nausea and Emesis after Modern Antiemetics", Cancer, 2004, vol. 100, pp. 2261-2268.
Hecht, J.R., et al., "Prolonged Nausea and Vomiting after High Dose Chemotherapy and Autologous Peripheral Stem Cell Transplantation in the Treatment of High Risk Breast Carcinoma", Cancer, 1997, vol. 79, pp. 1698-1702.
Hellewell, S.B., and Bowen, W.D., "A sigma-like binding site in rat pheochromocytoma (PC12) cells: decreased affinity for (+)-benzomorphans and lower molecular weight suggest a different sigma receptor form that of guinea pig brain*", Brain Research, 1990, pp. 244-253.
Herrstedt, J., et al., "Acute emesis moderately emetogenic chemotherapy", Support Care Cancer, 2005, vol. 13, pp. 97-103.
Hesketh, M., et al., "Proposal for classifying the Acute Emetogenicity of Cancer Chemotherapy", Journal of Clinical Oncology, 1997, vol. 15, pp. 103-109.
Hudzik, T., et al., "σ Receptor-mediated emetic response in pigeons: agonists, antagonists and modifiers", European Journal of Pharmacology, 1993, vol. 236, pp. 279-287.
Khouzam, H.R., et al. "Remission of Cancer Chemotherapy-Induces Emesis During Antidepressant Therapy with Nefazodone", Psychosomatic Medicine, 1998, vol. 60, pp. 89-91.
Koralewski, P., et al., "Effectiveness of cyproheptadine in the management of delayed vomiting after cisplatin-based chemotherapy and the assessment of the influence of cyproheptadine on quality of life", Chemotherapy Dept. Rydygier Memorial Hospital, Cracow, Poland, vol. 5, pp. 499-503.
Leitner, M.L., et al., "Regional variation in to ration of $\sigma_2$ to $\sigma_2$ binding in rat brain", European Journal of Pharmacology, vol. 259, pp. 65-69.
Mielke, S., et al., "Peripheral neuropathy: A persisting challenge in paclitaxel-based regimes", European Journal of Cancer, 2006, vol. 42, pp. 24-30.
Owens, N.J. et al., "Antiemetic efficacy of prochlorperazine, haloperidol, and droperidol in cisplatin-induced emesis", Clinical Pharmacy, 1984, vol. 3, pp. 168-170.
Palmer, J.L., and Fisch, M.J., "Association Between Symptoms Distress and Survival in Outpatients Seen in a Palliative Care Caner Center", Journal of Pain and Symptom Management, 2005, vol. 29, No. 6, pp. 565-571.
Park, S.B., et al., "Mechanisms Underlying Chemotherapy-Induced Neurotoxicity and the Potential for Neuroprotective Strategies", Current Medicinal Chemistry, 2008, vol. 15, pp. 3081-3094.
Prasad, P.D., et al., "Exon-Intron Structure, Analysis of Promoter Region, and Chromosomal Localization of Human Type 1 σ Receptor Gene", J. Neurochem, 1998, vol. 70, pp. 443-451.
Quiron, R., et al., "A Proposal for the classification of sigma binding sites", TIPS, 1992, vol. 13, pp. 85-86.
Raynov, J., "Antiemetics: Side effects and reactions", Archive of Oncology, 2001, vol. 9, No. 3, pp. 151-153.
Roila, F., et al., "Delayed emesis: moderately emetogenic chemotherapy", Support Care Cancer, 2005, vol. 13, pp. 104-108.
Ronsisvalle, G., et al., "Opioid and sigma receptor studies. New Developments in the design of selective sigma ligands*", Pure Appl. Chem., 2001, vol. 73, No. 9, pp. 1499-1509.
Selwood, D.L., et al. Synthesis and Biological Evaluation of Novel Pyrazoles and Indazoles as Activators of the Nitric Oxide Receptor, Soluble Guanylate Cyclase, J. Med. Chem, 2001, vol. 44,pp. 78-93.
Tramer, M.R., et al., "Efficacy and Adverse Effects of Prophylactic Antiemetics during Patient-Controlled Analgesia Therapy: A Quantitative Systematic Review," Anesth. Analg., 1999, vol. 88, pp. 1354-1361.
Wolf, S., et al., "Chemotherapy-induced peripheral neuropathy: Prevention and treatment strategies," European Journal of Cancer, 2008, vol. 44(11), pp. 1507-1515.
International Search report issued by the International Searching Authority (ISA/O.E.P.M.) on Aug. 31, 2011 in connection with International Applications No. PCT/EP2011/058224.
Hudzik et al. "Sigma receptor-mediated emetic response in pigeons: agonists, antagonists and modifiers", European Journal of Pharmacology, 1993, 236, pp. 279-287.
Hayashi T. and Su T-S. "Sigma-1 Receptor Ligands: Potential in the Treatment of Neuropsychiatric Disorders", CNS Drugs, 2004, 18(5), pp. 269-284.
Hudzik T.J., "Sigma Ligand-Induced Emesis in the Pigeon", Pharmacology Biochemistry & Behavior, 1991, 41(1), pp. 215-217.
Laggner C. et al., "Discovery of High-Affinity Ligands of σ1 Receptor, ERG2, and Emopamil Binding Protein by Pharmacophore Modeling and Virtual Screening", Journal of Medicinal Chemistry, 2005, 48, pp. 4754-4764.
Hahner M, Moebius FF, Flandorfer A, Knaus HG, Striessnig J, Kempner E, Glossmann H. Purification, molecular cloning, and expression of the mammalian sigmal-binding site. Proc Natl Aced Sci U S A. Jul. 23, 1996;93(15):8072-7.
Hayashi T, Su TP. Sigma-1 receptor ligands: potential in the treatment of neuropsychiatric disorders. CNS Drugs. 2004;18(5):269-84.
Jordan K, Kasper C, Schmoll HJ. Chemotherapy-induced nausea and vomiting: current and new standards in the antiemetic prophylaxis and treatment. Eur J Cancer. Jan. 2005;41(2):199-205.
Matsumoto RR1, Pouw B. Correlation between neuroleptic binding to sigma(1) and sigma(2) receptors and acute dystonic reactions. Eur J Pharmacol. Aug. 4, 2000;401(2):155-60.
Lippincott's Illustrated Review: Pharmacology, Richard Harvey, 5*th* edition published by Wolters Kluwer "Gastrointestinal and Antiemetic Drugs", pp. 351-362.

(56) References Cited

OTHER PUBLICATIONS

Luedtke RR, Perez E, Yang SH, Liu R, Vangveravong S, Tu Z, Mach RH, Simpkins JW. Neuroprotective effects of high affinity Σ1 receptor selective compounds. Brain Res. Mar. 2, 2012;1441:17-26.
Romero L, Zamanillo D, Nadal X, Sánchez-Arroyos R, Rivera-Arconada I, Dordal A, Montero A, Muro A, Bura A, Segalés C, Laloya M, Hernández E, Portillo-Salido E, Escriche M, Codony X, Encina G, Burgueño J, Merlos M, Baeyens JM, Giraldo J, López-García JA, Maldonado R, Plata-Salamán CR, Vela JM. Pharmacological properties of S1RA, a new sigma-1 receptor antagonist that inhibits neuropathic pain and activity-induced spinal sensitization. Br J Pharmacol. Aug. 2012;166(8):2289-306.
Seigel LJ, Longo DL. The Control of Chemotherapy-Induced Emesis. Ann Intern Med. 1981;95(3):352-359.
Smith JC, Wright EL. Haloperidol: An alternative butyrophenone for nausea and vomiting prophylaxis in anesthesia. AANA Journal 2005, vol. 73, No. 4, pp. 273-275.
Werling LL, Keller A, Frank JG, Nuwayhid SJ. A comparison of the binding profiles of dextromethorphan, memantine, fluoxetine and amitriptyline: treatment of involuntary emotional expression disorder. Exp Neurol. Oct. 2007;207(2):248-57.
Xu J, Zeng C, Chu W, Pan F, Rothfuss JM, Zhang F, Tu Z, Zhou D, Zeng D, Vangveravong S, Johnston F, Spitzer D, Chang KC, Hotchkiss RS, Hawkins WG,Wheeler KT, Mach RH. Identification of the PGRMC1 protein complex as the putative sigma-2 receptor binding site. Nat Commun. Jul. 5, 2011;2:380.
Nausea and Vomiting (PDQ)—Health Professional Version: Prevention and Management of Acute or Delayed Nausea and Vomiting (Emesis). National Cancer Institute <http://www.cancer.gov/about-cancer/treatment/side-effects/nausea/nausea-hp-pdq#section/_66>.
"Chemotherapy at home, pain and its treatment", Soins, Table Ronde, Office De Publicite Generale, Paris, FR, (19890901), No. 528, ISSN 0038-0814, pp. 17-20, XP009107313 [A] 1-16.
Abadias, M. et al. "Saftey, Tolerability and Pharmacokinetics of Single and Multiple Doses of a Novel Sigma-1 Receptor Antagonist in Three Randomized Phase I studies," British Journal of Clinical Pharmacology, 2012, 75:1, 103-117.
Abbott, C, A., et al., "The North-West Diabetes Foot Care Study: incidence of, and risk factors for, new diabetic foot ulceration in a community-based patient cohort", Diabetic Medicine, vol. 19, 2002, pp. 377-384.
Abraham, D.J., et al., "Burger's Medicinal Chemistry: Drug Discovery and Development" 7th edition, 8 vol. set, 2010.
Abrams, P., et al., "The standardisation of terminology of lower urinary tract function: report from the standardisation sub-committee of the International Continence Society", Neurology andUrodynamics, 21, 2002, pp. 167-178.
Acta Obstetrica Gynecologica Japonica, 2000, vol. 52 (6), pp. 117-120.
Advokat, C., et al., "Selective antinociceptive effect of excitatory amino acid antagonists in intact and acute spinal rats," Pharmacology Biochemistry and Behavior 51(4):855-60 1995.
Alberts, D.S., et al., "Cisplatin-associated neurotoxicity: can it be prevented?" Anti-cancer Drugs, 1995, vol. 6, pp. 369-383.
Almerico, AM., "1-Methyi-3H-pyrazolo[1, 2-a]benzo[1, 2, 3, 4] tetrazin-3-ones: Design, synthesis and biological activity of new antitumor agents", Journal of Medicinal Chemistry, vol. 48, 2005.
Anderson, B. D. et al., "Preparation of Water-Soluble Compounds Through Salt Formation" The Practice of Medicinal Chemistry, Chapter 34, pp. 739-754 (1996).
Angst, M.S., et al., "Opioid-induced Hyperalgesia: A Qualitative Systematic Review," Anesthesiology. vol. 104 No. 3, Sep. 2006, pp. 570-587.
Anonymous "Opioid-Induced hyperalgesia," http://1web.archive.org/web/20080712205531/http://en.wikipedia.org/wiki/opioid-inducedhyperalgesia (retrieved Feb. 16, 2017).
Anton, E., "Delayed toxicity of cyclophosphamide on the bladder of DBA/2 and C57BL/6 female mouse," Int. J. Exp. Path., 83, 2002, pp. 47-53.
Arafa, et al., Journal of Medicinal Chemistry, 2005, American Chemical Society, vol. 48, pp. 5480-5488.
Arthritis [online], [retrieved on Nov. 20, 2007]. Retrieved from the Internet, URL; http://www.nlm.nih.gov/medlineplus/ency/article/001243.htm>.
Asano, T., et al. Antinociception by epidural and systemic alpha (2) adrenoceptor agonist and their binding affinity in rat spinal cord and brain, Anesth Anal g. 2000; 90 (2): 400-407.
Baraldi, et al., "Ethyl 2, 4-Dioxalkanoates as Starting Materials for a Convenient Route to 3(2H)Furanones and 3(2H) Furanimines", Tetrahedron, vol. 43, No. 1, pp. 235-242, 1987.
Baraldi, et al., "Ethyl 5-Substituted-3-lsoxazolecarboxylates as Starting Materials for a Convenient Route to 3(2H) Furanones and 3(2H) Iminofuranes", Tetrahedron Lett., 25(38), pp. 4314-4316; 1984.
Batson, et al., "a-Hydroxy Cyclopentenones from a-Diketones", Organic Letters, vol. 7, No. 13, pp. 2771-2774, 2005.
Beaudegnies, R., et al., "Design and Synthesis of novel spirocyclopropyl cyclohexane-1, 3-diones and -1, 3, 5-triones for their incorporation into potent HppD inhibitors", Tetrahedron Letters, 2010, vol. 51, pp. 2741-2744.
Bennett, G. J. Pathophysiology and Animal Models of Cancer—Related Painful.
Peripheral Neuropathy, The Oncologist, 2010, 15 (supp12), pp. 9-12.
Bon, K., et al., "Characterization of cyclophosphamide cystitis, a model of visceral and refferes pain, in the mouse: species and strain differences." J UROL., (2003), vol. 170, No. 3, pp. 1008-1012.
Botting, R.M.; Clinical Infectious Diseases, 2000, 31, S202-10.
Boulton, A.J.M., et al., "Diabetic Neuropathies" Diabetes Care, vol. 28, No. 4, Apr. 2005, pp. 956-962.
Bowen W. D., Pharmaceutica Acta Helvetiae; 2000; 74:211-218.
Brennan, T.J., et al., "Characterization of a rat model of incisional pain", Pain, 1996, vol. 64, pp. 493-501.
Brussee, et al., Diabetes, 2008, 57: 1664-1673, "Distal Degenerative Sensory Neuropathy in a Long-Term Type 2 Diabetes Rat Model".
Bryans, J.S., et al., "3-substituted GABA analogs with central nervous system activity: a review," Med Res Rev, 19, 1999, pp. 149-177.
Bryans, J.S., et al., "Identification of novel ligands for the gabapentin binding site on the alpha-2-delta subunit of a calcium channel and their evaluation as anticonvulsant agents", J. Med. Chern. 41, 1998, pp. 1838-1845.
Bryant et al., Opioids and addiction: Emerging pharmaceutical strategies for reducing reward and opponent processes, Clinical Neuroscience Research, 2005, 5, pp. 103-115.
Buerkle, H., Yaksh, T. L. Pharmacological evidence for different alpha 2-adrenergic receptor sites mediating analgesia and sedation in the rat, Br J Anaesth. 1998; 81 (2): 208-215.
Bura, S.A. et al., "Evaluation of The Effect of The Selective Sigma-1 Receptor Antagonist SIRA in Neuropathic Pain Using an Operant Model", Eur J. Pain Supplements 2010, vol. 4, p. 49.
Buvanendran, A., et al. "Characterization of a New Animal Model for Evaluation of Persistent Postthoracotomy Pain", Anesth Analg, 2004, vol. 99, pp. 1453-1460.
Cancer [online], [retrieved on Jul. 6, 2007]. Retrieved from the Internet, URL: http://www.nim.nih. gov/medlineplus/cancer.html>.
Lala et al., "Role of Nitric Oxide in Tumor Progression: Lessons from Experimental Tumors," Cancer and Metastasis Reviews, 17(1), 91-106, 1998.
Cao, J. et al., "Dual Probes for the Dopamine Transporter and sigma1 Receptors: Novel Piperazinyl Alkyl-bis(4-ftuorophenyi)amine Analogues as Potential Cocaine-Abuse Therapeutic Agents", J. Med. Chem, 2003, pp. 2589-2598.
Carlsson, et al., "Interaction of pentobarbital and morphine in the tail-ftick test performed on rates: synergism at the spinal and antagonism at the supraspinal level", NeureSci. Lett.; 1986; 71; pp. 356-360.
Carrie, et al., Int Orthopaedics vol. 30, pase 445-451. publication year: 2006.
Carter, N., et al., "Duloxetine: a review of its use in the treatment of generalized anxiety disorder.", CNS Drugs 2009, (2009), vol. 23, No. 6, ISSN 1172-7047, pp. 523-541, ISSN: 1172-7047.
Case 07 "Joint Pain and Muscle Pain", Nurse Beans—Smart Nurse, Nov. 2007, vol. 9, No. II, pp. 1238-1239.

(56) References Cited

OTHER PUBLICATIONS

Celerier, et al., "Progressive Enhancement of Delayed Hyperalgesia Induced by Repeated Heroin Administration: a Sensitization Process," The Journal of Neuroscience. vol. 21, No. 11 pp. 4074-4080 (2001).

Cepeda, MS, "Comparison of Morphine, ketorolac, and their combination for postoperative pain: results form a large, randomized, double-blind trial", anesthesiology, 2005, vol. 103, No. 6, pp. 1225-1232.

Cersosimo, R.J., "Oxaliplatin-Associated Neuropathy: A Review", the Annals of Pharmacotherapy, 2005 vol. 39 pp. 128-135.

Chaplan S. R., et al., "Quantitative assessment of tactile allodynia in the rat paw", J. Neurosci. Methods, (1994), vol. 53, pp. 55-63.

Chaudhry, V., et al., "Bortezomib and thalidomide-induced subacute demyelinating polyneuropathy," Clinical Neurophysiology, 2009, vol. 120, p. e111.

Chaudhry, V., et al., "Peripheral Neuropathy from Taxol and Cisplatin Combination Chemotherapy: Clinical and Electrophysiological Studies", Annals of Neurology, 1994, vol. 35, No. 3, pp. 304-311.

Cheng, et al., Modern Bone Science, Modern Orthopaedics, "14.2.2 Drug Analgesia," p. 164, 2010, including English translation.

Chen, S.R., et al., "Synergistic Effect between Intrathecal Non-NMDA Antagonist and Gabapentin on Allodynia Induced by Spinal Nerve Ligation in Rats", Anesthesiology, 2000, vol. 92, pp. 500-506.

Chen, D., et al., "Development and application of rodent models for type 2 Diabetes", Diabetes, Obesity and Metabolism, vol. 7, 2005, pp. 307-317.

Cherny, N., "Opioids and the Management of Cancer Pain", Eur. J. Cancer Supplement 2005, vol. 3, pp. 61-75.

Chichenkov, O.N. et al., "Effect of haloperidol on the analgesic activity of intracisternally and intrathecally injected opiate agonists," Farmakologiya I Toksikologiya, (1985), vol. 48. 48, No. 4, pp. 58-61.

Chien, C., et al., "Sigma antagonists potentiate opioid analgesia in rats," Neuroscience Letters, vol. 190, No. 2, 1995, pp. 137-139.

Chien, et al., "Selective Antagonism of Opioid Analgesia by a Sigma System," J. Pharmacol. Exp. Ther.; 1994; 271; pp. 1583-1590.

Cited ref STN search abstract JP10055048. p. 8.

Clark, J.B., et al., "The Diabetic Zucker Fatty Rat (41611)", Proceedings of the society for experimental Biology and Medicine, 1983, vol. 173, pp. 68-75.

Cobos, E. J., et al., Pharmacology and therapeutic potential of Sigma(1) receptor ligands. Curr. Neuropharmacol. 2008; 6, 344-366.

Consilium MedSigma-receptors: new potentials of the treatment of depressions. Consilium Medicumicum 2012, vol. 14, no. 2 (found in the Internet: URL<new.Consiliummedicum.com/magazines/cm/medicum/article/21505, paragraphs 4-8).

Final Office Action dated Nov. 29, 2007 in related U.S. Appl. No. 10/978,250.

Final Office Action dated Oct. 20, 2008 in related Appl. No. 10/978,250.

Non-Final Office Action dated Apr. 16, 2008 in related U.S. Appl. No. 10/978,250.

Non-Final Office Action dated Jun. 14, 2007 in related U.S. Appl. No. 10/978,250.

Requirement for Restriction/Election dated Apr. 5, 2007 in related U.S. Appl. No. 10/978,250.

Coxon, et al., "Acid-catalysed Rearrangements of trans- and cis-1-Acetoxy-3,4-epoxypentane and 1-Acetoxy-4,5- epoxyhexane", J. Chem. Soc. Chem. Commun., 8, pp. 261-262, 1973.

D'Amour, F. E. And Smith, D. L. A method for determining the loss of pain sensation, J. Pharmacal. Exp. Ther. 1941; 72:74-79.

Dani, et al. (2007) The local antinociceptive effects of paracetamol in neuropathic pain are mediated by cannabinoid receptors. European Journal of Pharmacology 573(1-3): 214-215.

Danziger, et al., Automated Site-directed Drug Design: A General Algorithm for Knowledge Acquisition about Hydrogen-Bonding Regions at Protein Surfaces, Mar. 22, 1989, the Royal Society, Proceedings of the Royal Society of London. Series B, Biological Sciences, vol. 236, No. 1283, pp. 101-113.

Daousi, C., et al., "Chronic painful peripheral neuropathy in an urban community: a controlled comparison of people with and without diabetes", Diabetic Medicine, vol. 21, 2004, pp. 976-982.

Dapeng Ll "The Role of Glial Cells in . . . Pain", Thesis of Huazhong, University of Science and Technology, 2006, p. 24; Publication Date: Feb. 19, 2008.

Database WPI Week 200451 Thomson Scientific, London, GB; An 2004-529624-& JP 2004 196678 A (Dainippon Pharm Co Ltd) Jul. 15, 2004.

Dauben, W., et al., "Organic Reactions at High Pressure Preparation of Wittig Phosphonium Salts at Ambient Temperature", J. Org. Chern., 1984, vol. 49, pp. 4293-4295.

Davies, A., et al., Functional biology of the alpha-2-delta subunits of voltage-gated calcium.

channels, trends in Pharmacological Sciences, vol. 28, No. 5, 2007, pp. 220-228.

DeHaven-Hudkins, et al., "Characterization of the binding of [ H](+)-pentazocine to o recognition sites in guinea pig brain,"European Journal of Pharmacology—Molecular Pharmacology Section, 1992, vol. 227, pp. 371-378.

Dewar, "Diethyl-[3-(5-methyl-1-phenyl-1H-pyrazol-3-yl)-propyl]amine", Database Beilstein, Beilstein Institute for Organic Chemistry, Frankfurt-Main, DE, Database accession No. 213356, XP002605612 [X] 1-3,5,6,9.

Dewar, M. J. S., "Attempts to find new Antimalarials. Part XXI", Journal of the Chemical Society, (1944), pp. 615-619.

Dias, V. C., et al., Clinical experience with transdermal clonidine in African-American and Hispanic-American patients with hypertension: evaluation from a 12-week prospective, open-label clinical trial in community-based clinics, Am J Ther. 1999; 6 (1): 19-24.

Diaz, J.L. et al., "Selective Sigma-1 Receptor Antagonists: Emerging Target for the Treatment of Neuropathic Pain", Cent. Nerv. Syst. Agents in Med. Chem. 2009, vol. 9 pp. 172-183.

Diaz, J.L., et al., "Synthesis and Biological Evaluation of the 1-Arylpyrazole Class of sigma 1 Receptor Antagonists: Identification of 4-{2-[5-Methyl-1-(naphthaien-2-y1)-1 H - pyrazol-3-yloxy}ethyl]morpholine (S1RA, E-52862)", Journal of Medicinal Chemistry, (20121011), vol. 55, No. 19, doi:10.1021/jm3007323, ISSN 0022-2623, pp. 8211-8224, XP055094581 [Y] 1-14,16 * abstract * * p. 8219, col. left, Paragraphs 3-4.*

Dmitrieva, N., et al., "The role of nerve growth factor in a model of visceral inflammation", Neuroscience, vol. 78, No. 2, 1997, pp. 449-459.

Dosen-Micovic, et. al., Bioorganic and Medicinal Chemistry, 2006, Elsevier, vol. 14, pp. 2887-2895.

Dougherty, P.M., et al. "Taxol-induced sensory disturbance is characterized by preferential impairment of myelinated fiber function in cancer patients", Pain, 2004, vol. 109, pp. 132-142.

Drug encyclopedia M., RLS 2001, pp. 572-573, articles "Morphine", "Morphine Sulfate".

Du, J., et al. "Kainate-induced Excitation and Sensitization of Nociceptors in Normal and Inflamed Rat Glabrous Skin", Neuroscience, 2006, vol. 137, pp. 999-1013.

Dugowson, et al.; Phys. Med. Rehabil. Clin. N. Arn. 2006, 17, 347-354.

Dukic-Ott, A. "Production of pellets via extrusion spheronisation without the incorporation of microcrystalline cellulose: A critical review," European Journal of Pharmaceutics and Biopharmaceutics, 2009, vol. 71, pp. 38-46.

Dunlap, B., et al., "Chemotherapy-Induced Peripheral Neuropathy Measurement", The Journal of Supportive Oncology, 2006, vol. 4, 8, pp.

Dworkin R.H., "An Overview of Neuropathic Pain: Syndromes, Symptoms, Signs, and Several Mechanisms," The Clinical Journal of Pain 2002, vol. 18, pp. 343-349.

Dworkin, R.H. et al., "Recommendations for the Pharmacological Management of Neuropathic Pain: Literature Update", Mayo Clin. Proc., 2010, 85(3)(Suppl), S3-S14. 90.

(56) References Cited

OTHER PUBLICATIONS

Effenberger, F., et al., Chern. Ber., 102(10), 3260-3267, 1969.

Eghbaldar, et al., "Substances aromatisantes separation chirale par chromatographie gazeuse" Parfums, Cosmetiques, Aromes, 104, pp. 71-78, 1992.

Eisenach, J. C., et al., Intrathecal, but not intravenous, clonidine reduces experimental thermal or capsaicin-induced pain and hyperalgesia in normal volunteers; Anesth Analg; 1998; 87: 591-596.

Entrena, J.M., et al., "Sigma-I receptors are essential for capsaicin-induced mechanical hypersensitivity: Studies with selective sigma-1 ligands and sigma-1 knockout mice", Pain, (2009), vol. 143, pp. 252-261.

Epilepsy [online], [retrieved on Nov. 20, 2007]. Retrieved from the Internet, URL; http://www .nim.nih. gov /medlineplus/ ency/ article/000694.htm>.

Epstein, et al., "Oral Doxepin Rinse: The Analgesic Effect and Duration of Pain Reduction in Patients with Oral Mucositis Due to Cancer Therapy" (2006) Pain Medicine, vol. 103, No. 2, pp. 465-470.

Epstein, et al., "Oral topical doxepin rinse: analgesic effect in patients with oral mucosal pain due to cancer or cancer therapy" (2001) Oral Oncology, 37:632-637.

European Search Report dated Feb. 1, 2005 in connection with priorirty European Application No. Ep 04077421.8.

European Search Report dated Apr. 19, 2010 in connection with European Application No. EP10382024.7.

European Search Report dated Dec. 20, 2013 in connection with European Application No. EP13382246.0.

European Search Report dated Feb. 5, 2010 in connection with European Application No. EP09382144.

European Search Report dated Jan. 31, 2011 in connection European Patent Application no. 10382326.6.

European Search Report dated Jul. 1, 2010 in connection with European Patent Application No. EP10382025.

European Search Report dated Jun. 16, 2010 in connection with European Application No. EP 10382023.

European Search Report dated Mar. 11, 2011 in connection with European Application No. EP10382330.8.

European Search Report issued on Apr. 14, 2010 in connection with European Application No. EP09382261.

European Search Report dated May 3, 2013 in connection with European Patent Application No. EP13382140.

European Search Report dated Oct. 1, 2010 in connection with European Application No. EP10382215.1.

European Search Report dated Oct. 18, 2011 in connection with European Application No. EP11382157.3.

European Search Report dated Oct. 2, 2008 in connection with European Application No. EP 08380122.

European Search Report dated Oct. 29, 2010 in connection with European Application No. EP10382136.

European Search Report dated Sep. 12, 2008 in connection with European Application No. EP08384006.

Extended European Search report issued on Oct. 22, 2010 by European patent Office in connection with European Application No. EP 10 38 2148.

Falk et al. "Pain and Nociception: Mechanisms of Cancer-Induced Bone Pain", Journal Clinical Oncology, 2014, vol. 32, pp. 1647-1654.

Field, M.J., et al., "Identification of the alpha-2-delta-1 subunit of voltage-dependent calcium channels as a molecular target for pain mediating the analgesic actions of pregabalin", PNAS, vol. 103, No. 46, Nov. 14, 2006, pp. 17537-17542.

Finnerup, N.B. et al. "The evidence for pharmacological treatment of neuropathic pain", Pain, 2010, vol. 150, pp. 573-581.

Forsyth, P.A. et al., "Prospective study of paclitaxel-induced peripheral neuropathy with quantitative sensory testing", Journal of Neuro-Oncology, 1997, vol. 35, pp. 47-53.

Friedman, J.E., et al., Altered expression of muscle glucose transporter GLUT -4 in diabetic fatty Zucker rats (ZDF/Drtfa), American Physiological Society, 1991, E782-E788.

Gabriel, A.F., Preoperative housing in an enriched environment significantly reduces the duration of post-operative pain in a rat model of knee inflammation, Neurosci. Lett. 2010, vol. 469, No. 2, pp. 219-232.

Gauchan, P., et al., "Mechanical Allodynia Induced by Pacli taxel, oxaliplatin and Vincristine: Different Effectiveness of Voltage-Dependent Calcium Channel a26-1 subunit", Biol. Phann. Bull., 2009, vol. 32, No. 4 f pp. 732-734.

Gentili, M., et al., Intra-articular morphine and clonidine produce comparable analgesia but the combination is not more effective, Br J Anaesth. 1997; 79 (5): 660-661.

Glass et al., "Evaluation of pentamorphone in humans: a new potent opiate," Anesth. Analg. Mar. 1989, 68(3) 302-7.

Goblirsch, M.J., et al., "Biology of Bone Cancer Pain," Clin. Cancer Res. 2006' vol. 12 (20 Suppl.), pp. 6231s-6235s.

Goodman, et al., "The Pharmacological Basis of Therapeutics", 8th 13-18. 1992.

Gordois, A., et al., "The Health Care Costs of Diabetic Peripheral Neuropathy in the U.S.", Diabetes Care, vol. 26, No. 6, Jun. 2003, pp. 1790-1795.

Gordon, A.N., et al., "Phase 1 Dose Escalation of Paclitaxel in Patients with Advanced Ovarian Cancer Receiving Cisplatin: Rapid Development of Neurotoxicity is Dose-Limiting", Journal of Clinical Oncology, 1997, vol. 15, No. 5, pp. 1965-1973.

Grahame-Smith, D.G., et al., Oxford textbook on clinical pharmacology and drug therapy M., "Meditsina", 2000, pp. 658-661, Chapter "Narcotic analgesics".

Grover, S., et al., "Role of inflammation in bladder function and interstitial cystitis", Therapeutic Advances in Urology, 3(1), 2011, pp. 19-33.

Guignard B., et al. "Intraoperative Remifentanil Increses Postoperative Pain and Morphine Requirement" Advances in Urology, 3(1), 2011, pp. 19-33.

Guignard, et al., "Acute Opioid Tolerance: Intraoperative Remifentanilincreases Postoperative Pain and Morphine Requirement," Anesthesiology, vol. 93 pp. 409-417 (2000).

Haleblian, "Characterization of Habits and Crystalline of Solids and Their Pharmaceutical Applications," Journal of Pharmaceutical Sciences, vol. 64, No. 8 pp. 1269-1268.

Hammack, et al., "Phase III evaluation of nortriptyline for alleviation of symptoms of cis-platinum-induced peripheral neuropathy"(2002) Pain, 98:195-203. (Abstract).

Hancock, et al., "Characteristics and Significance of the Amorphous State in Phamnaceutical Systems," Journal of Phamnaceutical Sciences, vol. 86, No. 1 pp. 1-12 (1997).

Hanno, Philip, "International Consultation on IC—Rome, Sep. 2004/Forging an interenational consensus: progress in painful bladder syndrome/interstitial cystitis", Int Urogynocol J, 16, 2005, pp. S2-S34.

Harden, N., et al., "Unmet Needs in the Management of Neuropathic Pain", Journal of Pain and Symptom Management, 2003, 25, 5s, S12-S17.

Hartwig, J., Synthesis, Structure, and Reactivity of a Palladium Hydrazonato Complex: A New Type of Reductive Elimination Reaction to FormC-N Bonds and Catalytic Arylation.

Hellewell, S.B., et al., "A Sigma-likebinding site in rat pheochromocytoma (PC12) cells: decreased affinity for (+)-benzomorphans and lower molecular weight suggest a diffrent sigma receptor form from that of gunea pig brain", Brain Research, (1990) vol. 527, pp. 244-253.

Herndon, et al.; "Management of Chronic Nonmalignant Pain with Nonsteroidal Antiinflammatory Drugs", Pharmacotherapy, 2008, 28(6), 788-805.

Hidaka, T., et al., W5-7 "A Basic Study of the Effect Peony Licorice Water on Paclitaxel-Induced Pain in Mice", Japan Academic Journal of Cancer Treatment, Sep. 2009, vol. 44, No. 2, pp. 323 [inc. machine English language translation).

Hileman, G.A., et al., "Response surface optimization of high dose pellets by extrusion and spheronization," International Journal of Pharmceutics, 1993, vol. 100, pp. 71-79.

(56) References Cited

OTHER PUBLICATIONS

Hinz et al., "Dipyrone elicits substantial inhibition of peripheral cyclooxygenases in humans: new insights into the pharmacology of an old analgesic"FASEB Journal, 2007, 7, 2343-2351.
Hiranita, et al., "Reinforcing effects of sigma-receptor agonists in rats trained to self-administer cocaine," J Pharmacol Exp Ther. Feb. 2010; 332(2):515-524 (2010).
Narujo, Hiroyuki, et al., Cancer Pain Treatment—Clinical Oral Morphine Extended-Release Tablets (once/day), 5th, Pharma Medical, 2007, including English language translation.
Horner, et al., "Azo-aryle und Phenazine aus primaren Arylaminanionen durch Autoxydation", Chern. Ber, 96, pp. 786-793, 1963.
Hsu, et al., Toxic. Appl. Pharmac., vol. 73, No. 3, pp. 411-415, 1984.
IASP Classification of Chronic Pain, 2002, 2nd edition, pp. 201-213.
International Preliminary Report of Patentability with Written Opinion of the International Searching Authority dated Nov. 27, 2012 in connection with International Application No. PCT/EP2011/058633.
International Preliminary Report of Patentability with Written Opinion of the International Searching Authority dated Feb. 14, 2012 in connection with International Application No. PCT/EP2010/061720.
International Preliminary Report of Patentability with Written Opinion of the International Searching Authority dated May 30, 2012 in connection with International Application No. PCT/EP2010/068213.
International Preliminary Report of Patentability with Written Opinion of the International Searching Authority dated Feb. 12, 2013 in connection with International Patent Application No. PCT/EP2011/063583.
International Preliminary Report of Patentability with Written Opinion of the International Searching Authority dated Aug. 2012 in connection with International Application No. PCT/EP2011/051644.
International Preliminary Report of Patentability with Written Opinion of the International Searching Authority dated Aug. 2012 in connection with International Application No. PCT/EP11/51643.
International Preliminary Report of Patentability with Written Opinion of the International Searching Authority dated Aug. 24, 2010 in connection with International Application No. PCT/EP2009/001109.
International Preliminary Report of Patentability with Written Opinion of the International Searching Authority dated Dec. 29, 2015 in connection with International Application No. PCT/EP2014/063360.
International Preliminary Report of Patentability with Written Opinion of the International Searching Authority dated Feb. 28, 2007 in connection with International Application No. PCT/EP2005/009375.
International Preliminary Report of Patentability with Written Opinion of the International Searching Authority dated Feb. 3, 2013 in connection with International Application No. PCT/EP2011/063286.
Zheng, F.Y., et al. "The Response of Spinal Microglia to Chemotherapy Evoked Painful Peripheral Neuropathies Is Distinct From That Evoked by Traumatic Nerve Injuries," Neuroscience, 2011, 176, pp. 447-454.
International Preliminary Report of Patentability with Written Opinion of the International Searching Authority dated Jun. 21, 2016 in connection with International Application No. PCT/EP2014/077996.
International Preliminary Report of Patentability with Written Opinion of the International Searching Authority dated Jun. 21, 2016 in connection with International Application No. PCT/EP2014/077992.
International Preliminary Report of Patentability with Written Opinion of the International Searching Authority dated Jun. 4, 2013 in connection with International Application No. PCT/EP2011/071584.
International Preliminary Report of Patentability with Written Opinion of the International Searching Authority dated Jun. 2012 in connection with International Application No. PCT/EP2012/059232.
International Preliminary Report of Patentability with Written Opinion of the International Searching Authority dated Mar. 15, 2016 in connection with International Applications No. PCT/EP2014/069370.
International Preliminary Report of Patentability with Written Opinion of the International Searching Authority dated May 30, 2012 in connection with International Application No. PCT/EP2010/068256.
International Preliminary Report of Patentability with Written Opinion of the International Searching Authority dated Nov. 27, 2012 in connection with International Applications No. PCT/EP2011/058224.
International Preliminary Report of Patentability with Written Opinion of the International Searching Authority dated Oct. 26, 2010 in connection with International Application No. PCT/EP2009/054974.
International Preliminary Report of Patentability with Written Opinion of the International Searching Authority dated Oct. 20, 2015 in connection with International Application No. PCT/EP2014/057608.
International Search Report dated Jun. 17, 2009 in connection with International Application No. PCT/EP2009/054974.
International Search Report dated Jul. 24, 2009 in connection with International Application No. PCT/EP2009/054981.
International Search Report dated Jan. 31, 2012 in connection with International Application No. PCT/EP2011/063286.
International Search Report dated Apr. 5, 2011 in connection International Application No. PCT/EP2011/051644.
International Search Report dated Nov. 25, 2010 in connection with International Application No. PCT/EP2010/061720.
International Search Report dated May 4, 2011 in connection with International Application No. PCT/EP2011/051630.
International Search Report dated Aug. 31, 2011 in connection with International Application No. PCT/EP2011/063583.
International Search Report dated May 4, 2011 in connection International Application No. PCT/E22010/068256.
International Search Report dated Sep. 21, 2011 in connection with International Application No. PCT/EP2011/058633.
International Search Report dated Feb. 25, 2015 in connection with International Application No. PCT/EP2014/077996.
International Search Report dated Jan. 12, 2005 in connection with International Application No. PCT/EP2005/009375.
International Search Report dated Jan. 16, 2012 in connection with International Application No. PCT/EP2001/071583.
International Search report dated Jul. 7, 2009 in connection with International Application No. PCT/EP2009/001109.
International Search Report dated Jun. 26, 2012 in connection International Application No. PCT/EP12/59232.
International Search Report dated Mar. 13, 2012 in connection with International Application No. PCT/EP2011/071584.
International Search Report dated Mar. 23, 2011 in connection with International Application No. PCT/EP2010/068213.
International Search Report dated Mar. 6, 2014 in connection with International Application No. PCT/EP2014/057608.
International Search report dated May 23, 2011 in connection International Application No. PCT/EP11/51643.
International Search report dated Oct. 31, 2014 in connection with International Application No. PCT/EP2014/069370.
International Search report dated Sep. 17, 2014 in connection with International Application No. PCT/EP2014/063360.
International Search Report dated Sep. 3, 2015 in connection with International Application No. PCT/EP2014/077992.
International Search Report dated Mar. 8, 2011 in connection with International Applications No. PCT/EP2011/058224.
International Preliminary Report of Patentability with Written Opinion of the International Searching Authority dated Oct. 26, 2010 in connection with International Application No. PCT/EP2009/054981.

(56) References Cited

OTHER PUBLICATIONS

Isakov "The problem of pain in oncology", Russian Medicinal Journal 2000, vol. 17, pp. 723-727.
Isomers [on-line], [retrieved on Mar. 11, 2007]. Retrieved from the Internet, URL; http://chemed.chem.purdue.edu/genohem/topicreview/bp/lorganic/isomers .html>.
Izenwasser, S., et al., "Characterization of kappa-opioid receptor binding in human insular cortex", Life Sciences, Pergamon Press, Oxford, GB, vol. 65, No. 9, Jul. 23, 1999, pp. 857-862.
Janicki, et al., "Detection of Antagonist Activity for Narcotic Analgesics in Mouse Hot-Plate Test" Pharmacol. Biochem. Behavior, 1979; 10(4); pp. 623-626.
Jover, I., et al., "Evaluation, by a Statistically Designed Experiment, of an Experimental Grade of Microcrystalline Cellulose, Avicel 955, as a Technology to Aid to Production of Pellets with High Drug Loading," Journal of Pharmaceutical Sciences, 1996, vol. 85, No. 71 pp. 700-705.
Kaiser, et al., "Binding to the sigma receptor" Neurotransmissions; 1991; 7(1); 1-5.
Kautio, et al., "Amitriptyline in the Prevention of Chemotherapy—induced Neuropathic Symptoms" (2009) Anticancer Research, 29:2601-2606.
Kautio, et al., "Amitriptyline in the Treatment of Chemotherapy—induced Neuropathic Symptoms" (2008) Journal of Pain and Symptom Management, 35(1) :31-39.
Kawamata, M., et al. "Experimental incision-induced pain in human skin: effects of systemic lidocaine on flare formation and hyperalgesia", Pain, 2002, vol. 100, pp. 77-89.
Kehlet, H., et al. "Persistent Surgical Pain: Risk Factors and Prevention," Lancet, 2006, vol. 367; pp. 1618-1625.
Kehlet, H., et al. "PROSPECT: evidence-based, procedure-specific prostoperative pain management", Best Practice Res Clin Anaesthesiol., 2007, vol. 21, pp. 149-159.
Kehlet, H., et al., "Anaesthesia, surgery, and challenges in postoperative recovery", Lancet 2003, vol. 362, pp. 1921-1928.
Kadiroglu, A.K., et al., "The effect of venlafaxine HC1 on painful peripheral diabetic neuropathy in patients with type 2 diabetes mellitus.", Journal of Diabetes and Its Complications Jul.-Aug. 2008, (Jul. 2008), vol. 22, No. 4, ISSN 1873-460X, pp. 241-245, XP002721925 [Y] 1-17 * Venlafaxine HC1 is effective in the treatment of peripheral diabetic neuropathic pain*.
Kenakin, A., Pharmacology Primer, The Evolving Pharmacology of GPCR's, 2006, pp. 27-60.
Kerba, et al. Oct. 2010, Journal of Clinical Oncology, vol. No. 33, pp. 4892-4897.
Kest, et. al., Pharmacology Biochemistry, and Behavior, 1995, Pergamon, vol. 52, No. 1, pp. 175-178.
Khouzam, H. R., et al., "Remission of Cancer Chemotherapy-Induces Emesis During Antidepressant Therapy with Nefazodone", Psychosomatic Medicine, 1998, vol. 60, pp. 89-91.
Kim, et al., "Activation of the spinal sigma-1 receptor enhances NMDA-induced pain via PKC- and PKA-dependent phosphorylation of the Nri subunit in mice", Br. J. Pharmacal., 2008, vol. 154, pp. 1125-1134.
Kim, et al., "Update on the Pathology and Diagnosis of Interstitial Cystitis/Bladder Pain Syndrom: A Review"Int Neurourol J.; Mar. 2016; 20(1); 13-17.
Kirchmair, R., et al., "Therapeutic Angiogenesis Inhibits or Rescues Chemotherapy-induced Peripheral Neuropathy: Taxol-and Thalidomide-induced Injury of Vasa Nervorum is Ameliorated by VEGF," Molecular Therapy, 2005, vol. 151 No. 1, pp. 69-75.
Kranz, H., et al., "Drug Release from MCC- and carrageenan-based pellets: Experiment and theory," European Journal of Pharmaceutics and Biopharmaceutics, 2009, vol. 73, pp. 302-309.
Kuloor, et. al., Age and Aging, 2006, Oxford University Press, 35, pp. 639-640.
Kunz, N. R., et al., "Diabetic neuropathic pain management with venlafaxine extended release", European Neuropsychopharmacology, Elsevier Science Publishers BV, Amsterdam, NL, vol. 10, ISSN 0924-977X, (Sep. 1, 2000), p. 389, (Sep. 1, 2000), XP027389705 [Y] 1-17. * Venlafaxine controlled release is effective in the treatment of pain *.
Kuruvilla et al., Arch Otolaryngol Head Neck Surg. Jan. 2009; 135(1): 101-105.
Laboratoire Roger Bellon's CAS: 87: 5959, 1977.
LaBuda, et al., (2005) Pharmacological evaluation of the selective spinal nerve ligation model of neuroFathic pain in the rat. J. Neurosci. Methods 144 (2) : 175-181.
LaBudde, et al., "The Synthesis of the Mono- and Dihydroxy Derivatives of 1,2,5,6-Dibenzanthracene Excreted by the Rabbit and of other Hydroxylated Dibenzanthracene Derivatives", J. Am. Chern, Soc., 80, pp. 1225-1236, 1958.
Langa et al., "Generation and phenotypic analysis of sigma receptor type I (o1) Knowckout mice," European Journal of Neuroscience, 2003, vol. 18, pp. 2188-2196.
Laird, J., et al., Deficits in visceral pain and referred hyperalgesia in Nav1.8.
(SNS/PN3)-null mice, The Journal of Neuroscience, 22(19), Oct. 1, 2002, pp. 8352-8356.
Lang, M., et al., "The Use of Polymer Heteronuclei for Crystalline Polymorph selection,"Journal of the American Chemical Society, 2002, vol. 124, No. 50, pp. 14834-14835, s1-s2.
Lau, et al. (2010) Electroacupuncture versus celecoxib for neuropathic pain in rat SNL model. Neuroscience 170 (2): 655-661.
Le Bars, D., et al., Animal models of nociception, Pharmacal, Rev. 2001; 53, 597-652.
Lee, S., et al., "Large-Scale Aspects of Salt Formation: Processing of Intermediates and Final Products", Handbook of Pharmaceutical Salts: Properties, Selection, and use, 2002, Chapter 8, pp. 191-192, 211-214, Chapter 12, 265,266, 282-283.
Leitner et al., "Regional variation in the ratio of of to a2 binding in rat brain", European Journal of Pharmacology, vol. 259 pp. 65-69 (1994).
Levine, J.D. et al., "Desiperamide Enhances Opiate Postoperative Analgesia", Pain, 1986, vol. 27, pp. 45-49.
Li, et al., "Asymmetric Total Synthesis and Formal Total Synthesis of the Antitumor Sesquiterpenoid (+)-Eremantholide A", Organic Letters, vol. 9, No. 7, pp. 1267-1270, 2007.
Li, et al., "Synthesis and Structure-Antitumor Activity of 4,6-Diamino-1, 2-Dihydro-2, 2-Dimethyi-1-(Substituted Naphthyi-2)-1,3,5-Triazines", Chern. Res. Chinese Univ., 7(3), pp. 197-200, 1991.
Li, F., et al., "Taurine reverses neuroplogical and neurovascular deficits in Zucker diabetic fatty rats," Neurobiology of Disease, vol. 22, 2006, pp. 699-676.
Lowry, et al., "Protein measurement with the folin phenol reagent,"J. Bio.Chem, 1951, vol. 193, pp. 265-275.
Lugar N.M., et al., "Efficacy of systemic morphine suggests a fundarnen tal difference in the mechanisms that generate bone cancer vs. inflammatory oain", Pain 2002, vol. 99, pp. 397-406.
Lugar, N.M., et al., "Bone Cancer Pain: From Model to Mechanism to Therapy", J. Pain and Symp. Manag. 2005, vol. 29, pp. 832-846.
Lytle, et al., "Effects of long-term corn consumption on brain serotonin and the response to electic shock," Science vol. 190, pp. 692-694 (1975).
Mantyh, "Bone cancer pain: From mechanism to therapy", Opin. Support. Palliat. Care, 2014, vol. 8, pp. 83-90.
Mao, J., "Opiod-induced abnormal pain sensitivity: implications in clinical opiod therapy,"Pain. vol. 100 pp. 213-217 (2002).
Mar. 1, 2016 Fourth Office Action, issued in connection with Chinese Patent Application No. 201180065232.X, including English language translation.
Mar. 29, 2016 Office Action, issued in connection with Japanese Patent Application No. 2013-541369, including English translation.
Marks, D.M., et al., "Serotonin-Norepinephrine reuptake for pain control: Premise andpromise", Current Neuropharmacology, 2009, 7, pp. 331-336.
Maryanoff, B.E., et al., The Wittig Olefination Reaction and Modifications Involving Phosphoryl-Stabilized Carbanions. Stereochemistry, Mechanism, and Selected Synthetic Aspectsu, Chern. Rev., 1989, vol. 89, pp. 863-927.

(56) References Cited

OTHER PUBLICATIONS

Maurice, T., Su, T. P., The pharmacology ofSigma-1receptors. Pharmacal. Ther. 2009; 124, 195-206.
Max, M.B., et al. "Endogenous Monoamine Analgesic Systems: Amitriptyline in Painful Diabetic Neuropathy", Anesth. Prog., 1987, vol. 34, pp. 113-127.
McGill, J.B., et al., "13-Biocker use and diabetes symptom score: results from the GEMINI study", Diabetes, Obesity and Metabolism, vol. 9, No. 3, May 2007, pp. 408-417.
Mega, et al., Experimental Diabetes Research, Jan. 12, 2011, Diabetic Nephropathy Amelioration by a Low-Dose Sitagiiptin in an Animal Model of Type 2 Diabetes (Zucker Diabetic Fatty Rat).
Mei, et al., "Receptor Modulation of Opioid Analgesia in the Mouse", J. Pharmacol Exp. Ther.; 2002; 300(4); pp. 1070-1074.
Menten, J., "Co-analgesics and adjuvant medication in opioid treated cancer pain", Fur. J. Cancer Supplement 2005, vol. 3, pp. 77-86.
Merskey, H., et al., IASP, Classification of Chronic pain; 2nd Ed.; IASP Press (2002); 210-213.
Ming, L.C., "Screening Polymorphic Forms of Drug Substances by Generalized Crystallization Techniques," May 2007 (English language Translation of Abstract).
Moncada A., et al., Effects of serine/threonine protein inhibitors on morphine-induced antinociception in the tail flick test in mice. Eur J Pharmacal. 2003; Mar. 28; 465(1- 2): 53-60.
Mosandi, et al., "Stereoisomeric Flavor Compounds XLIV: Enantioselective Analysis of Some Important Flavor Molecules", J. High Resol. Chromatog 13(9), pp. 660-662, 1990.
Mouedden, et al., "Pharmacological evaluation of opioid and non-opioid analgesics in a murine bone cancer model of pain", Pharm. Biochem. And Behavior, 2007, vol. 86, pp. 458-467.
Mueller, et al., "Some Derivatives of 7-Methoxy- and 10-Methoxybenzo (f) quinoline", J. Am. Chem. Soc., 66, pp. 860-862, 1944.
Mukerji, et al., "Addition of Nitrile Oxides to Olefins, Synthesis of Dihydrojasmone and Starting Material for Prostanoids. A Novel Route to Pyrroles", Tetrahedron, 39 (13) pp. 2231-2235, 1983.
Nakajima K., et al., An increase in spinal cord noradrenaline is major contributor to the antihyperalgesic effect of antidepressants after peripheral nerve injury in the rat. Pain. 2012; 153 (5) : 990.
Nakazato A., et al., "Synthesis and SAR of 1-alkyl-2-phenylethylamine derivatives designed from N,Ndipropyl-4-methoxy-3-(2-phenylethoxy) phenylethylamine to discover ?lligands", J. Med. Chem., (1999), vol. 42, pp. 3965-3970.
Nieto, F. R., et al., "188 A New Selective Sigma-1 Receptor Antagonist (SIRA) Inhibits the Development and Expression of Neuropathic Pain Induced by Paclitaxel in Mice," European Journal of Pain Supplements, vol. 4, No. 1, 2010, p. 56.
Nieto, F.R., et al., "Tetrodotoxin inhibits the development and expression of neuropathic pain induced by paclitaxel in mice", Pain, 2008, vol. 137, pp. 520-531.
Niiyama, et al., "SB366791, a TRPV1 antagonist, potentiates analgesic effects of systemic morphine in a murine model of bone cancer pain", Br. J. Anaesth., 2009, vol. 102, pp. 251-258.
Noda, et al., "A Neuroactive Steroid, Dehydroepiandrosterone Sulfate, Attenuates the Development of Morphine Dependence: An Association with Signal Receptors," Neuroscience 2001 Abstract, Presentation No. 668.4, Nov. 2001.
Nomura, M., et al., "Studies on drug dependence (Rept 322): Attenuation of morphine- and psychostimulants-induced place preference by sigmal receptor agonist SA4503", Japanese Journal of Pharmacology, the Japanese Pharmacological Society, Kyoto, JP, vol. 79, No. suppl. 1, Jan. 1, 1999, p. 224P.
O'Brien, C. J., "Recycling the Waste: The Development of a Catalytic Witting Reaction", Agnew. Chem. Int. Ed. 2009, vol. 48, pp. 6836-6839.
Office Action and Search Report corresponding to Taiwanese Patent Application No. 100127236 (Translation) [undated].
Office Action dated Mar. 18, 2013 in connection with Russian Patent Application No. 2010138634, filed Feb. 17, 2009.
Official Action corresponding to Japanese Patent Application No. 2612013-523580, dated Mar. 31, 2015.
Ohsawa, et al., "Effect of acute topical application of(+)—pentazocine on the mechanical allodynia in diabetic mice" Eur. J. Pharmacal., 2010, 641, pp. 49-53.
Olivar, T., et al., "Cyclophosphamide cystitis in mice: behavioural characterisation and correlation with bladder inflammation", European Journal of Pain, 3, 1999, pp. 141-149.
Oltman, C.L., et al., "Progression of vascular and neural dysfunction in sciatic nerves of Zucker diabetic fatty and Zucker rats", Am. J. Physiol. Endocrinol. Metab., vol. 289, 2005, pages.
Oltman, C.L., et al., "Vascular and neural dysfunction in Zucker diabetic fatty rats: a difficult condition to reverse", Diabetes, Obesity and Metabolism, vol. 10, 2008, pp. 64-74.
Oltman, et al., "Treatment of Zucker diabetic fatty rats with AVE7688 improves vascular and neural dysfunction", Diabetes, Obesity and Metabolism, vol. 11, No. 3, 2009, pp. 223-233.
O'Neill, J., et al., Unravelling the mystery of capsaicin: a tool to understand and treat pain. Pharrnacol Rev. Oct. 2012;64(4).
Ongioco, C. D., et al., Alpha2-adrenergic receptors in human dorsal root ganglia: predominance of alpha2b and alpha2c subtype mRNSs, Anesthesiology 2000; 92 (4): 968-976.
Osipova, N. A., "Tramadol (Tramal) in the Treatment of Acute and Chronic Pain Syndromes," Russky Meditsinsky Zhurnal (Russian Medical Journal), Feb. 25, 2003, No. 4, Sections: Pulmonology: Selected Lectures for Family Physicians (Retrieved from the Internet: URL <rmj.ru/number.36.htm).
Otto, et al., Pain Medicine, 2011, 12: 437-450, "Longitudinal Study of painful Diabetic Neuropathy in the Zucker Diabetic Fatty Rat Model of Type 2 Diabetes: Impaired Basal G-Protein Activity Appears to Underpin Marked Morphine Hyposensitivity at 6 Months.".
Pacharinsak,C., et al., "Animal Models of Cancer Pain", Comparative Medicine, 2008, vol. 58, No. 3, pp. 220-233.
Paice, J. A., "Clinical Challenges: Chemotherapy-induced Peripheral Neuropathy", Seminars in Oncology Nursing, 2009, vol. 25, No. 2, Suppl 1, pp. S8-S19.
Perret, D., et al., "Targeting voltage-gated calcium channels for pain rnanagernent", Neurotherapeutics: The Journal of the American Society for Experimental Neurotherapeutics, vol. 6, Oct. 2009, pp. 679-692.
Petrie, C. et al., "A Novel Biotinylated Adenylate Analogue Derived from Pyrazolou3,4-D 3/4 Pyrimidine for Labeling DNA Probes "Bioconjugate Chemistry, ACS, Washington, DC, US LNKD-DO1:10.1021/BC00012A011, vol. 2, No. 6, Nov. 1, 1991 (Nov. 1, 1991), pp. 441-446, XP0005727891SSN: 1043-1802.
Pirim, A., et al., "Addition of ketamine infusion to patient controlled analgesia with intravenous morphine after abdominal hysterectomy" Agri 2006 Jan; 18(1):52-8 Abstract.
Polomano, R.C. , et al., "Chemotherapy-evoked Painful Peripheral Neuropathy", Pain Medicine, 2001, vol. 2, No. 1, pp. 8-14.
Polomano, R.C., et al., "Pain and neuropathy in cancer survivors: Surgery, radiation, and chemotherapy can cause pain; research could improve its detection and treatment", Cancer Lippincott-Raven Pub., Hagerstown, MD, US, (Mar. 1, 2006), vol. 29, No. 2, suppl, ISSN 0162-220X, pp. 39-47, XP009107315 [A] 1-16 * p. 41, col. R, paragraph 2 * * page 42, col. R, paragraph 2 *.
Poncelet, A.N., "Risk factors, patterns of presentation, diagnosis, and treatment", Geriatrics, vol. 58, No. 6, Jun. 2003, pp. 16-18, 24-30.
Postma, T.J., et al., "Paclitaxel-induced neuropathy," Annals of Oncology, 1995, vol. 6, pp. 489-494.
Price, et al., J. Am. Chem. Soc., (2005), vol. 127, p. 5512.
Prodrug [online], [retrieved on Mar. 11, 2007. Retrieved from the Internet, URL; http://en.wikipedia.org/wiki/Prodrug>.
Puente, B., et al., "Sigma-1 receptors regulate activity-21 induced spinal sensitization and neuropathic pain after peripheral nerve injury", Pain, 2009, vol. 145, pp. 294-303.
Puskas, F.,et al., Intrathecal clonidine and severe hypotension after cardiopulmonary bypass, Anesth Analg. 2003; 97 (5): 1251-1253.
Quasthoff, S., et al., "Chemotherapy-induced peripheral neuropathy," J Neural., 2002, vol. 249, pp. 9-17.

(56) References Cited

OTHER PUBLICATIONS

Quirion, et al., "A proposal for the classification of sigma bonding sites," Trends Pharmacol. Sci., 1992 vol. 13, pp. 85-86.
Radesca, et al., "Synthesis and Receptor Binding of Enantimeric -Substituted cis-N-[2(3,4 Dishlorophenyl)ethy1]-2-(1-pyrrolidinyl) cyclohexylamines as High-Affinity oReceptor Ligands," J. Med. Chem., 1991, vol. 34, pp. 3058-3065.
Rao, R.D., et al., "Efficacy of Lamotrigine in the Management of Chemotherapy-induced Peripheral Neuropathy placebo-controlled trial, N01C3", Cancer; 2008, 112(12), 2802-2808.
Receveur, Jean-Marie, et al., "Synthesis and biological evaluation of conformationally restricted gabapentin analogues", Bioorganlc & Medicinal Chemistry Letters, 9, 1999, pp. 2329-2334.
Reuben, S. S., et al., "Evaluation of efficacy of the perioperative administration of venlafaxine XR in the prevention of postrnastectomy pain syndrome", Journal of Pain and Syrnptorn Management, Feb. 2004, vol. 27, No. 2, pp. 133-139.
Rodriguez-Spongy B., et al., "General principles of solid polymorphism: a supramolecular Perspective," Advanced Drug Delivery Reviews, vol. 56 (2004) pp. 241-274.
Roh, D., et al., "Intrathecal Injection of the 01 Receptor Antagonist BD1047 Blocks Both Mechanical Allodynia and Increases Spinal NR1 Expression during the Induction Phase of Rodent Neuropathic Pain", Anesthesiology, 2008, vol. 109, No. 5, pp. 879-889.
Romero, L., et al., J. Pharmacological properties of S1RA, a new Sigma-1 receptor antagonist that inhibits neuropathic pain and activity-induced spinal sensitization. Br. J. Pharmacal. 2012; doi: 10.1111/j.1476-5381.
Roos, et al., Radiotherapy and Oncology, 2003, vol. 67, pp. 207-212.
Rossiter, et al., "Copper (H)-Mediated Arylation with Aryl Boronic Acids for the N-Derivatization ofPyrazole Libraries," J. Comb. Chern., 2004, vol. 6, pp. 385-390, published on web Feb. 5, 2004.
Rouleau, A., et al., "Anti-inflammatory and antinociceptive properties of BP 2-94, a histamine H3-receptor agonist prodrug", The Journal of Pharmacology and Experimental Therapeutics, vol. 295, No. 1, 2000, pp. 219-225.
Rowinsky, E.K. et al., "Phase I and Pharmacologic Study of Paclitaxel and Cisplatin with Granulocyte Colony-25 Stimulating Factor: Neuromuscular Toxicity is Dose-Limiting", Journal of Clinical Oncology, 1993, vol. 11, No. 10, pp. 2010-2020.
Rowinsky, E.K., et al., "Clinical Toxicities Encountered 24 with Paclitaxel (TAXOL) ", Seminars in Oncology, 1993, vol. 20, No. 4, suppl. 3, pp. 1-15.
Sabetkasaie, M., et al., "Clonidine and guanfacine-induced antinociception in visceral pain: possible role of alpha2/I2 binding sites", European Journal of Pharmacology, Elsevier Science, NL, (Oct. 6, 2004), vol. 501, No. 1-3, doi:10.1016/J.Ejphar.2004.08.010, ISSN 0014-2999, pp. 95-101.
Saha, et al., "Spinal Mitogen-Activated Protein Kinase (MKP-3) Is Necessary for the Normal Resolution of Mechanical Allodynia in a Mouse Model of Acute Postoperative Pain", J.Neurosci., 2013, vol. 43, pp. 17182-17187.
Said, G., "Diabetic Neuropathy", Proceedings advanced studies in vol. 1, No. 11, Dec. 2001, pp. 457-459.
Sakurada T., et al., Differential effects of intraplantar capsazepine and ruthenium red on capsaicin-induced desensitization in mice. Pharmacal Biochern Behay. Apr. 2003; 7 5 (1): 1 15-21.
Sampson, C., et al., "Effects of imidazoline I2 receptor ligands on acute nociception in rats." Neuroreport Jan. 25, 2012, (Jan. 25, 2012), vol. 23, No. 2, ISSN 1473-558X, pp. 73-77, XP009169909 [Y] 1-15 * See abstract: imidazoline I2 receptor ligands have antinociceptic effect in acute pain *.
Samso, E., et al., Comparative assessment of the anaesthetic and analgesic effects of intramuscular and epidural clonidine in humans, Can J Anaesth. 1996; 43 (12): 1195-1202.
Sanchez-Fernandez, C., et al., "Potentiation of morphine-induced mechanical antinociception by sigma-1 receptor inhibition: role of peripheral sigma-1 receptors", Neuropharmacology, 70, 2013, pp. 348-358.
Sandford, M., et al., "Opioid Induced Hyperalgesia: Clinical Implications for the Pain Practitioner". Pain Physician 2009; 12:679-684.
Sant et al., "The mast cell in interstitial cystitis: role in pathophysiology and pathogenesis,"Urology, 69, Suppl 4A, 2007, pp. 34-40.
Schiff, et al., "Promotion of microtubule assembly in vitro by taxol". Nature (1979) vol. 277 pp. 665-667.
Schlegel, T., et al., "Responsiveness of C-fiber nociceptors to punetate force-controlled stimuli in isolated rat skin: lack of modulation by inflammatory mediators and flurbiprofen" Neuroscience Letters, vol. 361, 2004, pp. 163-167.
Zahn, P.K., et al., "Mechanisms for Pain Caused by Incisions", Anesthesia and Pain Medicine, 2002, vol. 271 No. 5, pp. 514-516.
Schoeffter, et al., "Functional, endogenously expressed 5-hydroxytryptamine 5-ht7 receptors in human vascular smooth muscle cells," British Journal of Pharmacology, 1996, vol. 117, pp. 993-994.
Schreiber, S., et al., "The antinociceptive effect of venlafaxine in mice is mediated through opioid and adrenergic mechanisms", Neuroscience Letters, Limerick, IE, (Jan. 1, 1999), vol. 273, doi: 10.1016/S0304-3940(99)00627-8, ISSN 0304-3940, pp. 85-88, XP003009174 [Y]1-17 * Venlafaxine has antinociceptive effects and is effective for treating pain *.
Gotub et al., "Molecular Classification of Cancer: Class Discovery and Class Prediction by Gene Expression Monitoring," Science, 286: 531-537, 1999.
Sevcik, M.A., et al., "Jlnti-NGF therapy profoundly reduces bone cancer pain and the accompanying increase in markers of peripheral and central sensitization", Pain 2005, vol. 115, pp. 128-141.
Shaw, et al., Proc. Soc. Exp. Biol. Med., (1983), vol. 173, No. 1, pp. 68-75.
Shen, D.M., et al., "Versatile and Efficient Solid-Phase Syntheses of Pyrazoles and Isoxazoles", Organic Letters, 2000, vol. 2, No. 18, pp. 2789-2792.
Shimizu, I., et al., "Effects of AH-9700, (+)-pentazocine, DTG and oxybutynin on micturition in anesthetized rats with acetone-induced cystitis", Life Sciences 69, 2001, pp. 1691-1697.
Shimoyama, E., et al., Integrative Medicine you Need to know now "Cancer and Integrative Medicine Palliative Medicine", Modern Physician, Nov. 2008, vol. 28, No. 11, pp. 1605-1607 [inc. machine English language translation].
Shu, et al., "Parameter Effects on the Thermal Reaction of Cystine and 2,5-Dimethyl-4-hydroxy-3(2H)-furanone", ACS Symposium Letters, 409, pp. 229-241, 1989.
Shvidenko, K.V., et al., "Recyclizatioh Reactiens of 2-(1-Benzoylpyrrolidin- 2-Ylidene) Malononitrile", 2010, vol. 46, No. 1, pp. 56-60.
Siau, C., et al., "Dysregulation of Cellular Calcitt.rn Homeostasis in Chemotherapy-Evoked Painful Peripheral Neuropathy", Anest :h Analg., 2006, 102(5), pp. 1485-1490.
Sierralta, F., et al., Alpha-Adrenoceptor and opioid receptor modulation of clonidine-induced antinociception, Br J Pharmacal. 1996; 119 (3) : 551-554.
Silvererman, M., "Opioid Induced Hyperalgesia: Clinical Implications for the Pain Practitioner," Pain Physician. vol. 12, pp. 679-684 (2009).
Sima, A.A.F., "The heterogeneity of diabetic neuropathy", Frontiers in Bioscience, May 2008, pp. 4809-4816.
Sima, A.A.F., et al., "A comparison of diabetic polyneuropathy in Type II diabetic Bbzdr/Wor rats and in Type I diabetic BBNVor rats", Diabetologia, vol. 43, 2000, pp. 786-793.
Smith, et al., "Paclitaxel-induced neuropathic hypersensitivity mice: Responses in 1 0 inbred mouse strains, "Life Sci., (2004), vol. 74, No. 21, pp. 2593-604.
Smith, M.T., "Opioid-induced hyperalgesia, opioid rotation and opioid combinations," Acute Pain. vol. 10, pp. 199-200 (2008) [Abstract].
Snyder, et al., "Receptor Mechanisms in Antipsychotic Drug Action: Focus on Sigma Receptors," Journal of Neuropsychiatry, Winter 1989, Vol , No. 1, pp. 7-15.
Sonal, G., et al., "Role of inflammation in bladder function and interstitial cystitis" Ther. Adv. Urol., (2011), vol. 3, No. 1, pp. 19-33.

(56) References Cited

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227.
Stahl, P.H., et al., "Monographs on Acids and Bases", Handbook of Pharmaceutical Salts: Properties, Selection, and Use, 2002, pp. 265-266, 282-283.
Non-Final Office Action issued on Feb. 2, 2009 in related U.S. Appl. No. 11/574,361 citing STN-search report report JP10055048 (p. 8).
Strupp, et al., "Transdermal fentanyl during high-dose chemotherapy and autologous stem cell support" (2000) Oncology Reports, 7:659-661.
Stubblefield, et al., "Upper-Extremity Pain Disorders in Breast Cancer" (2006) Arch Phys Med Rehabil, vol. 87, Suppl 1, pp. S96-599.
Su, et al., "The pharmacology of sigma-1 receptors" Pharmacology Therapeutics, vol. 124, pges 195-206, 2009.
Sussman, N., "SNRis versus SSRis: Mechanisms of action in treating depression and painful physical symptoms", Primary Care Companion J. Ciin. Psychiatry, 2003, 5 (suppl 7), pp. 19-26.
Suzuki, Y., et al., "Lowered response threshold and increased responsiveness to mechanical stimulation of cutaneous nociceptive fibers in streptozotocin-diabetic rat skin in vitro—correlates of mechanical allodynia and hyperalgesia observed in the early stage of diabetes", Neuroscience Research, vol. 43, 2002, pages.
Tanda, S., et al., "Pains Resistant to Opioids, and Countermeasures thereof ~ Including Peripheral Neuropathy Measures of Oxaliplatin", Pharmacy, Oct. 2007, vol. 58, No. 11, pp. 2947-2953 [inc. machine English language translation].
Taylor, C.P., "Mechanisms of analgesia by gabapentin and pregabil—calcium channel alpha2-delta [Ca v alpha2-delta]ligands", Pain, 142, 2009, pp. 13-16.
Telleria-Diaz, et al., "Spinal antinociceptive effects of cyclooxygenase inhibition during inflammation: involvement of prostaglandins and endocannabinoids". Pain, 2010, 148, pp. 26-35.
Theoharides, T.C., "Mast cell involvement in interstitial cystitis: a review of human experimental evidence," Urology, (2001), vol. 57, No. 6, pp. 47-55.
Tietze, L., et al., "Improved Synthesis of (E)-3-Alkoxy- and (E)-3-Phenoxyacryloyi Chlorides". Synthesis, (11), 1079-1080, 1993.
Trescot et al., "Opioids in the Management of Chronic Non-Cancer Pain: An Update of American Society of the Interventional Pain Physicians' (ASIPP) Guidelines," Pain Physician. Opioids Special Issue: 11 pp. S5-S62 (2008).
Uchitel, O.D., et al., "Acute modulation of calcium currents and synaptic transmission by Gabapentinoids," Channels, 4:6, Nov./Dec. 2010, pp. 490-496.
Van De Merwe, J.P., et al., "Diagnostic criteria, classification, and nomenclature for painful bladder syndrome/interstitial cystitis: an ESSIG proposal", European Urology, 53, 2008, pp. 60-67.
Vedejs, E., "Stereochemistry and Mechanism in the Wittig Reaction," Topics in Stereochemistry, 1994, vol. 21, pp. 1-157.
Velucci, "Heterogeneity of Chronic Pain", Clin. Drug Invest. 32 Suppl. 1, pp. 3-10.
Venturello, C., "2-Arylazo-2, 5-dimethyl-3-oxo-2, 3-dihydrof urans useful intermediates in the synthesis of 1- aryl-5-methyl-3-pyrazolones", Synthesis, 1979, pp. 283-287.
Venturello, C., et al., "A Novel Synthesis of Pyrazol-3-ones Form Biacetyl Dimer and Arenediazonium Salts", Journal of the Chemical Society, Perkin Transactions 1: Organic and Bio-organic Chemistry, (1972-1999), 7, 681-685, 1978.
Vileikyte, L., et al., Psychological aspects of diabetic neuropathic foot complications: an overview, Diabetes/Metabolism Research and Reviews, 2004, vol. 20 (Suppll), pp. S13-S18.
Vinik, A., et al., "Diabetic neuropathies: clinical and current treatment options". Nature Clinical Practice Endocrinology & Metabolism, (2006), 2(5):269-81.
Vippagunta, et al., "Crystalline solids," Advanced Drug Delivery Reviews, 48: 1-26, 2001.

Virmani, et al., Indian Journal of Chemistry, Section B:Organic Chemistry Including Medicinal Chemistry,vol. 17, 1979, pp. 472-477.
Virmani, V. et al., "Methyl-{3-[5-(4-nitro-phenyl)-1-phenyl-1H-pyrazol-3-yl]propyl}-amine", Database Beilstein, Beilstein for Organic Chemistry, Frankfurt-Main, De, Database accession No. 705147, XP002605613 [X] 1-3,9.
Virmani, V. et al., "Methyl-{4-[5-(4-nitro-phenyl)-1-phenyl-1H-pyrazol-3-yl]-butyl}amine", Database Beilstein, Beilstein Institute for Organic Chemistry, Frankfurt-Main, DE, Database accession No. 706821, XP002605614 [X] 1-3,9.
Virmani, V. et al., "Methyl-15-[5-(4-nitro-phenyl)-1-phenyl-1H-pyrazol-3-yl]-pentyl)-amine", Database Beilstein, Beilstein Institute for Organic Chemistry, Frankfurt-Main, DE, Database accession No. 710983, XP002605615 [X] 1-3,9.
Vorobeychik, et al., "Combination Therapy for Neuropathic Pain—A Review of Current Evidence," CNS Drugs, 2011, pp. 1-12.
Wagaw, S. et al., "A Palladium-Catalyzed Strategy for the Preparation of Indoles: A Novel Entry Into the Fischer Indole Synthesis", J. American Chemical Society, 1998, vol. 120, pp. 6621-6622.
Walker, et al., "Sigma Receptors: Biology and Function," Pharmacological Review, 1990, vol. 42, No. 4, pp. 355-402.
Wang, "Opioid-induced hyperalgesia", Chinese Journal of Pain Medicine, 14(3), pp. 129-130 (2008).
Wantuch, C., et al., "Pharmacological validation of a model of cystitis pain in the mouse", Neuroscience Letters, 421, 2007, pp. 250-252.
Wasserheit, C., et al., "Phase II trial of paclitaxel and cisplatin pain in women with advanced breast cancer: an active regimen with limiting neurotoxicity", Journal of Clinical Oncology, 1996, vol. 14, No. 7 pp. 1993-1999.
Weetman, A.P., "Graves' hyperthyroidism: how long should antithyroid drug therapy be continued to achieve remission?," Nature Clinical Practice Endocrinology and Metabolism, vol. 2, No. 1, Jan. 2006, pp. 2-3.
Whittington, C.M., et al., Understanding and utilizing mammalian venom via a platypus venom transcriptome. J. Proteomics 2009; 72; 155-164.
Wickham, "Chemotherapy-Induced Peripheral Neuropathy: A Review and Implications for Oncology Nursing Practice" (2007) Clinical Journal of Oncology Nursing, vol. 11, No. 3, pp. 361-376.
Wild, S., et al., "Global Prevalence of Diabetes", Diabetes Care, 27, No. 5, May 2004, pp. 1047-1053.
Wilkes, G. "Peripheral Neuropathy Related to Chemotherapy", Seminars in Oncology Nursing, 2007, vol. 23, 3. pp. 162-173.
Wilson, S. G., "The heritability of antinociception: common pharmacogenetic mediation of five neurochemically distinct analgesics," J Pharmacal Exp Ther. 2003; 304 (2): 547-559.
Winkler, et al., "Synthesis of Highly Functionalized Furanones via Aldol Reaction of 3-Silyloxyfurans", Organic Letters, vol. 7, No. 3, pp. 387-389, 2005.
Wolf, S., et al., "Chemotherapy-induced peripheral neuropathy: Prevention and treatment strategies," European Journal of Cancer, 2008, vol. 44, issue 11, pp. 1507-1515.
Wong, H.Y., et al., Pentarnorphone for Management of postoperative Pain. Anesth Analg. 1991; 72:656-60.
Wu, et al. Regulatory Perspectives of Type II Prodrug Development and Time—Dependent Toxicity Management: Nonclinical Pharm/Tox Analysis and the Role of Comparative Toxicology, Toxicology, 236: 1-6, 2007.
Wunsch, et al., "The $o_1$ Receptor Antagonist S1RA is a Promising Candidate for the Treatment of Neurogenic Pain". Journal Med. Chem. vol. 55, No. 19, pp. 8209-8210, 2012.
Xiaoping, et al., "Involvement of the spinal NMDA receptor/PKCy signaling 12 pathway in the development of bone cancer pain", brain Research, 2010, vol. 1335, pp. 83-90.
Yaksh, T. L., Pharmacology of spinal adrenergic systems which modulate spinal nociceptive processing. Pharmacal Biochem Behav. 1985; 22(5): 845-58.
Yasuda, M., et al., "Mast Cell Stabilization Promotes Antinociceptive Effects in a Mouse Model of Postoperative Pain," J. Pain Res., 2013, vol. 6, pp. 161-166.

(56) References Cited

OTHER PUBLICATIONS

Yeretzian, et al., "Analysing the headspace of coffee by proton-transfer-reaction mass-spectrometry", Int. J. Mass Spect, 223-224 (1-3), pp. 115-139, 2003.

* cited by examiner

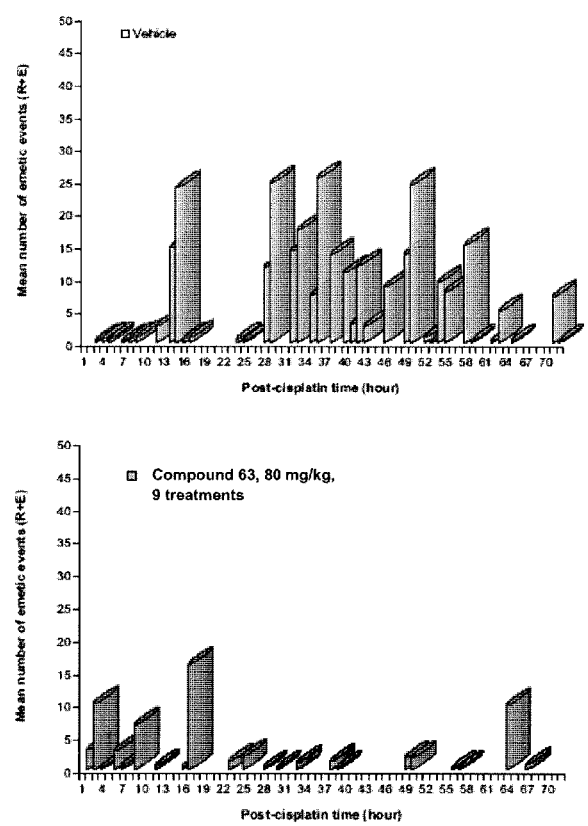

SIGMA LIGANDS FOR THE PREVENTION AND/OR TREATMENT OF EMESIS INDUCED BY CHEMOTHERAPY OR RADIOTHERAPY

This application is a §371 national stage of PCT International Application No. PCT/EP2011/058224, filed May 20, 2011, claiming priority of European Patent Application EP 10382136.9, filed May 21, 2010, the contents of all of which are hereby incorporated by reference into this application.

FIELD OF THE INVENTION

The present invention relates to the use of sigma receptor ligands in the prevention and/or treatment of emesis resulting from chemotherapy or radiotherapy. The present invention also refers to a combination of a sigma receptor ligand and a chemotherapeutic agent, for its use in the prevention and/or treatment of cancer while preventing or reducing emesis developing as a consequence of chemotherapy or radiotherapy.

BACKGROUND

Cancer and its associated therapies are some of the biggest health concerns in the world. The two main forms of treatment for cancer are chemotherapy and radiotherapy.

Chemotherapy, in combination with or as an alternative to surgery, is the method of choice in most cases for controlling or helping patients struck by carcinomas. Chemotherapy is defined as the use of chemical substances to treat disease and, in the sense of this invention, refers primarily to the use of cytotoxic or cytostatic drugs, called chemotherapeutic drugs, to treat cancer. In general it is a systemic treatment. Chemotherapy in cancer treatment consists of a personalized combination of potent chemotherapy drugs, designed to slow rapid cancer tumor growth, shrink tumors, kill cancer cells, and prevent the spread of cancer. The chemotherapeutic drugs prevent cells from replicating in the typical, out-of-control manner in which cancer cells divide.

Radiotherapy (or radiation therapy), on the other hand, involves the targeted use of ionizing radiation in cancer treatment. Radiotherapy is also commonly used in combination with other methods such as chemotherapy.

Anti-cancer therapy, such as the use of radiation or the administration of chemotherapeutic agents, is associated with Adverse Events including radio and chemotherapy-associated toxicities. Such toxicities and/or side-effects can materially offset or limit the potential benefits to the patient undergoing treatment, for example, resulting in treatment delays, treatment interruptions, dose modifications, dose schedule modifications, or even complete cessation of treatment. Thus, in addition to their adverse pharmacological affects, the development of said toxicities can limit or curtail the effectiveness of the primary treatment of the patient's cancer or preclude it all together. Cessation, interruption, or delays in patient treatment, or reducing the dosage of chemotherapeutic therapy or the fractions of radiotherapy, for example, may be detrimental to a subject's chances of long-term survival or control of the cancer, since such alterations in the treatment can allow the progression of cancer within the subject.

Emesis is a well-known and frequent side-effect of cancer chemotherapeutic agents, such as cisplatin, as well as of radiotherapy. It causes serious problems, and in some patients emesis is so severe that therapy must be discontinued. Anti-emetic agents are therefore often administered in order to alleviate this side-effect of the cancer chemotherapeutic agent or radiation. The anti-emetic agents employed are usually benzamide derivatives, such as metoclopramide, which have dopamine antagonist activity. In view of their dopamine antagonist activity benzamide derivatives such as metoclopramide themselves exhibit serious and undesirable side-effects, such as extra-pyramidal effects, i.e. tardive dyskinesia, acute dystonia, akathisia and tremor. Other anti-emetic drugs include 5-HT3 antagonists, e.g., ondansetron; corticosteroids, e.g., dexamethasone; and NK1 antagonists, e.g., aprepitant. These treatments fail to adequately address the needs of the patient. Serious side effects that may occur due to the use of antiemetics include fever, hearing loss, extreme nausea, constipation, ringing ears, severe stomach pain, severe vomiting, heartburn and unusual weight gain. Allergic reaction marked by swelling of the face or throat may also occur as a result of using antiemetics. Other less-serious side effects that may occur as a result of using antiemetics include darkening of the stool or tongue, drowsiness, dry mouth, mild nausea, stomach pain and headache.

Several reports on the drawbacks of anti-emetic drugs have been published. Although there is no consensus on the severity of said drawbacks such as the side effects, it is commonly agreed that they must be mitigated. In this sense, J. Raynov [Archive of Oncology 2001; 9(3):151-3] studies the side effects and reactions caused by antiemetics in patients under chemotherapy treatment and concludes that the most common side effects (extrapyramidal reactions, headache, constipation . . . ) are usually mild and controlled by symptomatic treatment, but they have to be identified by the medical staff and the patients.

The efficacy and adverse effects of known antiemetics (droperidol, ondasetron, hyoscine TTS, tropisetron, metoclopramide, propofol, promethazine) during Patient-Controlled Analgesia Therapy, a highly emetogenic treatment, has also been evaluated [Martin R. Tramèr et al. (Anaesth Analg 1999; 88: 1354-61)]. Although the results must be confirmed and completed, the authors state regarding droperidol that the risk of adverse effects is dose-dependent. Likewise, 5-HT$_3$ receptor antagonists (ondasetron, tropisetron) shown no evidence of any antinausea effect.

On another front, it is known in the art that neuropathic pain, allodynia, hyperalgesia, and especially, peripheral neuropathy, develop in a considerable number of cases as a result of chemotherapy. These are very specific symptoms arising from the neurotoxicity of the chemotherapeutic drug. The treatment of these symptoms is crucial for preserving the quality of life of the afflicted patients (Mielke et al., *Eur. J. Cancer,* 2006, 42(1), 24-30; Park et al., *Curr. Med. Chem.,* 2008, 15(29), 3081-94; Argyriou et al., *Blood,* 2008, 112(5), 1593-9). Unfortunately, an effective treatment for chemotherapy-induced peripheral neuropathy has yet to be found (Wolf et al., *Eur. J. Cancer,* 2008, 44(11), 1507-15). WO 2009/103487 and co-pending application EP 09382144.5 relates to the use of sigma receptor ligands in the prevention or treatment of pain resulting from chemotherapy.

In view of the above, an effective treatment for emesis that minimizes or eliminates one or more of this side effect of currently available cancer therapies is highly desirable. Therefore, there is an urgent need to provide a new form of treatment and/or prevention for the emesis associated to chemotherapy or radiotherapy. Preferably, the therapy should also be useful for treating and/or preventing other conditions developed as result of chemotherapy or radiotherapy, such as pain induced by chemo- or radiotherapy.

BRIEF DESCRIPTION OF THE INVENTION

The inventors of the present invention have surprisingly found and demonstrated for the first time that the administration of sigma receptor ligands is highly effective for preventing or treating the emesis developing as a consequence of chemotherapy or radiotherapy. Even more surprisingly, this invention demonstrates that the co-administration of these sigma ligands and a chemotherapeutic drug prevents the emesis frequently associated to chemotherapy or radiotherapy. This benefit of the invention is more evident when the sigma ligand is specifically a sigma receptor antagonist in the form of a (neutral) antagonist, an inverse agonist or a partial antagonist. An additional advantage and relating to WO 2009/103487 and the co-pending application EP 09382144.5 is the use of the sigma ligands, at the same time, in the prevention and/or treatment of pain induced by chemotherapy or radiotherapy. Accordingly, sigma ligands are useful against the two main concerns relating to chemotherapy and radiotherapy: pain and emesis induced.

Therefore, one aspect of the present invention relates to a sigma ligand for use in the prevention and/or treatment of emesis induced by chemotherapy or radiotherapy.

In a preferred embodiment, said sigma ligand has the general formula (I):

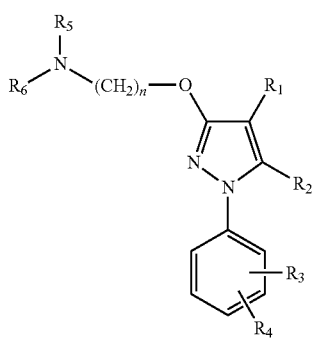

wherein
- $R_1$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;
- $R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_8$—$R_8$, —$NR_8R_9$, —$NR_8C(O)R_9$, —$NO_2$, —$N=CR_8R_9$, and halogen;
- $R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen, or together they form an optionally substituted fused ring system;
- $R_5$ and $R_6$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen, or together form, with the nitrogen atom to which they are attached, a substituted or unsubstituted, aromatic or non-aromatic heterocyclyl group;
- n is selected from 1, 2, 3, 4, 5, 6, 7 and 8;
- t is 1, 2 or 3;
- $R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted, aromatic or non-aromatic heterocyclyl, substituted or unsubstituted alkoxy, substituted or unsubstituted aryloxy, and halogen;
- or a pharmaceutically acceptable salt, isomer, prodrug or solvate thereof.

Another aspect of this invention refers to the use of a sigma receptor ligand as defined above for the manufacture of a medicament for the prevention and/or treatment of emesis induced by chemotherapy or radiotherapy.

Another aspect of the invention refers to a combination of at least one sigma ligand as defined above and at least one chemotherapeutic drug for use in the treatment of cancer and simultaneous prevention and/or treatment of emesis induced by chemotherapy or radiotherapy.

Another aspect of the invention relates to the use of a combination as defined above for the manufacture of a medicament for the treatment of cancer and simultaneous prevention and/or treatment of emesis induced by chemotherapy or radiotherapy.

Another aspect of the invention is a method of treatment of a patient, notably a human, suffering from emesis induced by chemotherapy or radiotherapy, or likely to suffer emesis as a result of a chemotherapeutic or radiotherapeutic treatment, which comprises administering to the patient in need of such a treatment or prophylaxis a therapeutically effective amount of a sigma ligand as defined above.

In a particular embodiment, sigma ligands are useful at the same time against the two main concerns relating to chemotherapy and radiotherapy: pain and emesis induced. Accordingly, a combination comprising at least a sigma ligand and at least one chemotherapeutic drug may be indicated for the treatment of cancer and simultaneous prevention and/or treatment of emesis and pain induced by chemotherapy or radiotherapy.

These aspects and preferred embodiments thereof are additionally also defined in the claims.

BRIEF DESCRIPTION OF THE FIGURES

FIG. 1: Mean number of emetic events per 1-hour epoch after Cisplatin administration (Mean+sem, n=4); vehicle vs compound 63 (80 mg/kg, 9 treatments)

The following abbreviations are used in the figures:
(R+E): retchings and expulsions
Mean: arithmetic mean
Sem: standard error of the mean
n=4: number of animals per group

DETAILED DESCRIPTION OF THE INVENTION

In the context of the present invention, the following terms have the meaning detailed below.

"Alkyl" refers to a straight or branched hydrocarbon chain radical consisting of 1 to 12 carbon atoms, containing no unsaturation, and which is attached to the rest of the molecule by a single bond, e. g., methyl, ethyl, n-propyl, i-propyl, n-butyl, t-butyl, n-pentyl, etc. Alkyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkyl radicals have from 1 to 6 carbon atoms. If substituted by aryl, it corresponds to an "Arylalkyl" radical, such as benzyl or phenethyl. If substituted by heterocyclyl, it corresponds to a "Heterocyclylalkyl" radical.

"Alkenyl" refers to a straight or branched hydrocarbon chain radical consisting of 2 to 12 carbon atoms, containing at least one unsaturation, and which is attached to the rest of the molecule by a single bond. Alkenill radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkenyl radicals have from 2 to 6 carbon atoms.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple aromatic ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —$OR_a$ where $R_a$ is an alkyl radical as defined above, e. g., methoxy, ethoxy, propoxy, etc.

"Aryloxy" refers to a radical of the formula —$OR_a$ where $R_a$ is an aryl radical as defined above, e. g., phenoxy, naphthoxy, etc.

"Amino" refers to a radical of the formula —$NH_2$, —$NHR_a$ or —$NR_aR_b$, optionally quaternized, wherein Ra and Rb are independently an alkyl or aryl radical as defined above, e.g., methylamino, ethylamino, dimethylamino, diethylamino, propylamino, phenylamino, etc.

"Halogen", "halo" or "hal" refers to bromo, chloro, iodo or fluoro.

References herein to substituted groups in the compounds of the present invention refer to the specified moiety that may be substituted at one or more available positions by one or more suitable groups, e. g., halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts" or "pharmaceutically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are preferred particularly, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate. A preferred solvate is the hydrate.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

Any compound that is a prodrug of a sigma ligand, in particular a prodrug of a compound of formula (I), is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley), "Design and Applications of Prodrugs" (H. Bundgaard ed., 1985, Harwood Academic Publishers) and Krogsgaard-Larsen et al. "Textbook of Drug design and Discovery" Taylor & Francis (April 2002).

Any compound referred to herein is intended to represent such specific compound as well as certain variations or forms. In particular, compounds referred to herein may have asymmetric centres and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The sigma ligands, in particular the compounds of formula (I), or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As noted previously, the term "pharmaceutically acceptable salts, solvates, prodrugs" refers to any salt, solvate, or any other compound which, upon administration to the recipient is capable of providing (directly or indirectly) a compound as described herein. However, it will be appreciated that non-pharmaceutically acceptable salts, solvates and prodrugs also fall within the scope of the invention since those may be useful in the preparation of pharmaceutically acceptable salts, solvates and prodrugs. The preparation of salts, solvates and prodrugs can be carried out by methods known in the art.

As used herein in regards to emesis, the terms "treat", "treating" and "treatment" include the eradication, removal, reversion, alleviation, modification, or control of emesis induced by chemotherapy or radiotherapy.

As used herein, the terms "prevention", "preventing", "preventive", "prevent" and prophylaxis refer to the capacity of a therapeutic to avoid, minimize or difficult the onset or development of a disease or condition before its onset, in this case emesis induced by chemotherapy or radiotherapy.

The above terms "treat" and the like as well as "prevent" and the like are also used with respect to the other diseases referred to in the present invention, i.e. cancer and pain.

As used herein, the terms "chemotherapy" or "chemotherapeutic drug" refer broadly to the use of a chemical drug for the treatment of cancer, tumors or malign neoplasia. Examples of chemical drugs used to treat cancer are cytostatic and cytotoxic drugs, but not limited only to these.

"Developing as a consequence of chemotherapy" or "resulting from chemotherapy" according to this invention is defined as: a) developing after or with at the beginning of chemotherapy and b) thus coinciding with or following the use of a chemotherapeutic drug. Therefore, the symptom to be treated is likely to be caused by or is due to the toxicity, cytotoxicity or especially, the peripheral neurotoxicity, of the chemotherapeutic drug.

As used herein, the terms "radiotherapy" or "radiation therapy" refer broadly to the use of ionizing radiation in cancer treatment to control malignant cell. It includes its use for curative, adjuvant or palliative purposes.

"Developing as a consequence of radiotherapy" or "resulting from radiotherapy" according to this invention is defined as developing after or with at the beginning of radiotherapy.

As mentioned above, chemo- and radiotherapy can be combined and therefore the emesis and/or pain resulting in such cases may be due to the action of one or both the chemotherapeutic drug and the radiation.

As used herein, the terms "emetic syndrome", "emetic condition", "vomiting", "nausea" and "emesis" are interchangeable and intended to have the same meaning. Emetic syndromes are those characterized by the reflexive act of ejecting the contents of the stomach through the mouth, or the feeling that such a reflexive action is likely to occur. Emetic conditions are often associated with chemotherapeutic treatment (chemotherapy-induced nausea and vomiting (CINV)) or surgery (post-operative nausea and vomiting (PONV)).

According to general knowledge chemotherapy-induced nausea and emesis (vomiting) (CINV) can be classified as follows:

Acute nausea and emesis which occurs during first 24 hours (day 1) after chemotherapy drug administration;
Delayed nausea and emesis which occurs from 24 hours after chemotherapy drug administration and may persist during some days (days 2 to 5); and
Anticipatory nausea and emesis which occurs prior to a chemotherapy drug administration as result of classical conditioning (also known as Pavlovian or respondent conditioning).

Emetic syndromes resulting from radiotherapeutic treatment can be classified analogously.

For bibliographic references relating to the emesis classification, see for example: Herrstedt J, Koeller J M, Roila F. Acute emesis: moderately emetogenic chemotherapy. *Supp Care Cancer.* 2005; 13: 97-103; Roila F, Warr D, Clark-Snow R A. Delayed emesis: moderately emetogenic chemotherapy. *Supp Care Cancer.* 2005; 13: 104-8; Aapro M, Molassiotis A, Olver I. Anticipatory nausea and vomiting. *Supp Care Cancer.* 2005; 13: 117-21.

Delayed nausea and emesis, which may appear even in the absence of acute nausea and emesis, remain important targets for improved therapeutic intervention (Grunberg S M, Deuson R R, Mavros P, et al.; *Cancer;* 100 (10); 2261-8, 2004).

According to the present invention, acute emesis occurs within about 16 hours of receiving chemotherapy, and delayed emesis occurs between about 18 hours and about 72 hours of receiving chemotherapy.

The term "cancer symptom burden" is used as a measure of a cancer subject's quality of life or the amount of amelioration of advanced cancer symptoms. A subject's cancer symptom burden may be measured by the Anderson Symptom Assessment System (ASAS).

The severity of overall cancer symptom burden or emetic conditions can be characterized by a number of scales that are known in the art. For example, the Anderson Symptom Assessment System (ASAS) is a modified form of the Edmonton Symptom Assessment System that includes an assessment of pain, fatigue, nausea, depression, anxiety, drowsiness, shortness of breath, appetite, sleep and feeling of wellbeing (see, Palmer et al. (2005) J. Pain and Symptom Management 6:565-571). ASAS requires patients to identify the severity of each of these symptoms on a 0-10 scale, with 0=none (or best), and 10=most (or worst imaginable). A subject ASAS score is the sum total of their numerical answers for the ten symptoms.

Alternatively, the Hesketh scale can be used to classify the acute emetogenicity of cancer chemotherapy (Hesketh et al. (1997) J. Clin. Oncology 15:103-109). The Hesketh scale sets forth five levels of emetogenicity. Level 1 consists of agents that are nonemetogenic; Level 2 consists of agents that cause vomiting in 10-30% of patients; Level 3 consists of agents that are moderately emetogenic with 30-60% of patients experiencing emesis; Level 4 consists of agents that produce emesis in 60-90% of patients; and Level 5 consists of agents that cause vomiting in >90% of patients.

As used herein, the terms "sigma ligand" or "sigma receptor ligand" refer to any compound binding to the sigma receptor. As stated previously, the sigma ligand is preferably a sigma receptor antagonist in the form of a (neutral) antagonist, an inverse agonist or a partial antagonist.

An "agonist" is defined as a compound that binds to a receptor and it has an intrinsic effect, and thus, increases the basal activity of a receptor when it contacts the receptor. An "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding.

A "partial antagonist" is defined as a compound that binds to the receptor and generates an antagonist response; however, a partial antagonist does not generate the full antagonist response. Partial antagonists are weak antagonists, thereby blocking partially the action of an agonist or inverse agonist on the receptor.

An "inverse agonist" is defined as a compound that produces an effect opposite to that of the agonist by occupying the same receptor and, thus, decreases the basal activity of a receptor (i.e., signaling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist.

"The sigma receptor/s" as used in this application is/are well known and defined using the following citation: this binding site represents a typical protein different from opioid, NMDA, dopaminergic, and other known neurotransmitter or hormone receptor families" (G. Ronsisvalle et al. Pure Appl. Chem. 73, 1499-1509 (2001)). Pharmacological data based on ligand binding studies, anatomical distribution and biochemical features distinguish at least two subtypes of or receptors (R. Quiron et al., Trends Pharmacol. Sci. 13, 85-86 (1992); M. L. Leitner, Eur. J. Pharmacol. 259, 65-69 (1994); S. B. Hellewell and W. D. Bowen; Brain Res. 527, 244-253 (1990)) (G. Ronsisvalle et al. Pure Appl. Chem. 73, 1499-1509 (2001)). The protein sequences of the sigma receptors (Sigma 1 (σ1) and Sigma 2 (σ2)) are known in the art (e.g. Prasad, P. D. et al., J. Neurochem. 70 (2), 443-451 (1998)). They show a very high affinity to various analgesics (e.g. pentazocine).

"Compound/s binding to the sigma receptor" or "sigma ligand" as used in this application is/are defined as a compound having an $IC_{50}$ value of 5000 nM, more preferably ≤1000 nM, more preferably 500 nM on the sigma receptor. More preferably, the $IC_{50}$ value is ≤250 nM. More preferably, the $IC_{50}$ value is ≤100 nM. Most preferably, the $IC_{50}$ value is ≤50 nM. The half maximal inhibitory concentration (IC50) is a measure of the effectiveness of a compound in inhibiting biological or biochemical function. The IC50 is the concentration of competing ligand which displaces 50% of the specific binding of the radioligand. Additionally, the wording "Compound/s binding to the sigma receptor", as used in the present application is defined as having at least ≥50% displacement using 10 nM radioligand specific for the sigma receptor (e.g. preferably [$^3$H]-(+)pentazocine) whereby the sigma receptor may be any sigma receptor subtype. Preferably, said compounds bind to the sigma-1 receptor subtype.

Compounds binding to the sigma receptor, generally also referred to as sigma ligands, are well known in the art. Many of them are encompassed by the "Compound's binding to the sigma receptor" definition above. Although there are many known uses for sigma ligands, such as antipsychotic drugs, anxiolytics, antidepressants, stroke treatment, antiepileptic drugs and many other indications, including antimigraine and general pain, there is no mention in the art of these compounds as useful for the treatment of the symptoms of emesis developing as a consequence of chemotherapy or radiotherapy.

Table 1 lists some sigma ligands known in the art (i.e. having an $IC_{40}$≤5000 nM). Some of these compounds may bind to the sigma-1 and/or to the sigma-2 receptor. These sigma ligands also include their respective salts, bases, and acids.

TABLE 1

| | |
|---|---|
| (−)-Cyanopindolol hemifumarate | Cutamesine hydrochloride |
| (−)-(1R,2S)-cis-N-[2-(3,4-Dichlorophenyl)ethyl]-2-pyrrolidinocyclohexylamine | Cyclobenzaprine HCl |
| (−)-1-[1-(3-Chlorophenyl)pyrrolidin-2-ylmethyl]-4-(2-phenylethyl)piperazine | Cycloheximide |
| (−)-Sparteine sulfate pentahydrate | Cyproheptadine HCl |
| (+)-Himbacine | Darrow Red HCl |
| (±)-1-Cyclohexyl-4-[3-(5-methoxy-1,2,3,4-tetrahydronaphthalen-1-yl)propyl]piperazine | Demecarium Bromide |
| (1S,5R)-3-[2-(2-Adamantyl)ethyl]-1,8,8-trimethyl-3-azabicyclo[3.2.1]octane hydrochloride | Denatonium Benzoate |
| (2-Dibutylamino-Ethyl)-Carbamic Acid 2-(4-Benzofuran-2-Ylmethyl-Piperazin-1-Yl)-Ethyl Ester | Deptropine Citrate |
| (4-[1,2,3]Thiadiazol-4-Yl-Benzyl)-Carbamic Acid 1-(3-Methoxy-2-Nitro-Benzyl)-Piperidin-3-Ylmethyl Ester | Desloratadine |
| (4aalpha,8aalpha)-6-(4-Fluorophenyl)-2-(4-pyridylmethyl)-6-hydroxydecahydroisoquinoline; (4a,8a-cis)-6-(4-Fluorophenyl)-2-(pyridin-4-ylmethyl)perhydroisoquinolin-6-ol | Dexbrompheniramine Maleate |
| (4aalpha,8abeta)-2-Benzyl-6-(4-fluorophenyl)-6-hydroxydecahydroisoquinoline | Dexchlorpheniramine Maleate |
| (6aR,9R)-5-Bromo-7-methyl-N-(2-propynyl)-4,6,6a,7,8,9-hexahydroindolo[4,3-fg]quinoline-9-carboxamide | Dexfenfluramine HCl |
| (S)-(−)-N-(2-Amino-3-phenylpropyl)-2-(3,4-dichlorophenyl)-N-methylacetamide hydrochloride | Dicyclomine HCl |
| (S)-Methamphetamine HCl | Diethylpropion HCl |
| [1-(9-Ethyl-9H-Carbazol-3-Ylmethyl)-Pyrrolidin-3-Yl]-Carbamic Acid 1-(3-Benzyloxy-4-Methoxy-Benzyl)-Piperidin-3-Ylmethyl Ester | Dimethisoquin HCl |
| [1-(9-Ethyl-9H-Carbazol-3-Ylmethyl)-Pyrrolidin-3-Yl]-Carbamic Acid 2-(Tert-Butoxycarbonyl-Naphthalen-1-Ylmethyl-Amino)-Ethyl Ester | Dimetindene Maleate |
| [4-(4-Ethyl-3,5-Dimethyl-Pyrazol-1-Yl)-Phenyl]-[4-(3-Phenyl-Allyl)-Piperazin-1-Yl]-Methanone | Diphemanil Methylsulfate |
| 1-(1,2-Diphenylethyl)Piperidine Maleate, (+/−) | Diphenidol HCl |
| 1-(1,4-Ethano-1,2,3,4-tetrahydro-2-naphthylmethyl)-4-methylpiperazine hydrate; 1-(Benzobicyclo[2.2.2]octen-2-ylmethyl)-4-methylpiperazine hydrate | Diphenoxylate HCl |
| 1-(1-Adamantyl)-2-[4-(2H-naphtho[1,8-cd]isothiazol-2-ylmethyl)piperidin-1-yl]ethanone S,S-dioxide hydrochloride | Diphenylpyraline HCl |
| 1-(1-Naphthyl)Piperazine HCl | Dipropyldopamine HBr |
| 1-(2-Benzyloxyethyl)-4-(3-phenylpropyl)piperazine dihydrochloride | Doxepin HCl |

TABLE 1-continued

| | |
|---|---|
| 1-(2-Phenylethyl)piperidine oxalate | Dyclonine HCl |
| 1-(3-Chlorophenyl)Piperazine HCl | Ebastine |
| 1-(3-Chlorothien-2-yl)-2-[4-(4-fluorobenzyl)piperidin-1-yl]ethanol | Econazole Nitrate |
| 1-(4-Bromo-Benzenesulfonyl)-4-(2-Tert-Butylsulfanyl-Benzyl)-Piperazine | Epinastine HCl |
| 1-(4-Chloro-3-hydroxyphenyl)-2-[4-(4-fluorobenzyl)piperidin-1-yl]ethanol | Ethaverine HCl |
| 1-(4-Chlorophenyl)-3-(hexahydroazepin-1-ylmethyl)pyrrolidin-2-one | Ethopropazine HCl |
| 1-(4-Chlorophenyl)-3(R)-[4-(2-methoxyethyl)-1-piperazinylmethyl]pyrrolidin-2-one (−)-D-tartrate | Eticlopride HCl, S(−)- |
| 1-(4-Chlorophenyl)-3(R)-[4-(2-methoxyethyl)piperazin-1-ylmethyl]pyrrolidin-2-one dihydrochloride | Etofenamate |
| 1'-(4-Fluorobenzyl)-1,3-dihydrospiro[2-benzofuran-1,4'-piperidine] | Etonitazenyl Isothiocyanate |
| 1-(4-Fluorophenyl)-4-[4-(5-fluoro-2-pyrimidinyl)-1-piperazinyl]butan-1-ol hydrochloride | Femoxetine HCl |
| 1-(4-Fluorophenyl)-4-[4-(5-fluoropyrimidin-2-yl)piperazin-1-yl]butan-1-ol; 1-[4-(4-Fluorophenyl)-4-hydroxybutyl]-4-(5-fluoropyrimidin-2-yl)piperazine | Fenfluramine HCl |
| 1'-(4-Phenylbutyl)spiro[1,3-dihydroisobenzofuran-1,4'-piperidine] | Fenticonazole Nitrate |
| 1-(Cyclobutylmethyl)-2-[3-phenyl-2(E)-propenyl]pyrrolidine hydrochloride | Fipexide HCl |
| 1-(Cyclohexylmethyl)-3'-methoxy-5'-phenyl-4',5'-dihydro-3'H-spiro[piperidine-4,1'-pyrano[4,3-c]pyrazole] | Flavoxate HCl |
| 1-(Cyclopropylmethyl)-4-[2-(4-fluorophenyl)-2-oxoethyl]piperidine hydrobromide | Flunarizine diHCl |
| 1,4-Bis[spiro[isobenzofuran-1(3H),4'-piperidin]-1'-yl]butane | Fluoxetine Related Compound B |
| 1-[(1R,3R)-2,2-Dimethyl-3-(2-phenoxyethyl)cyclobutylmethyl]piperidine | Fluperlapine |
| 1-[2-(3,4-Dichlorophenyl)ethyl]-3-(pyrrolidin-1-yl)piperidine | Fluphenazine Decanoate DiHCl |
| 1-[2-(3,4-Dichlorophenyl)ethyl]-4-(3-phenylpropyl)piperazine | Fluphenazine Enanthate DiHCl |
| 1-[2-(3,4-Dichlorophenyl)ethyl]-4-methylpiperazine | Fluphenazine HCl |
| 1-[2-(4-Fluorophenyl)ethyl]-4,4-dimethylhexahydroazepine hydrochloride | Fluphenazine N-Mustard DiHCl |
| 1-[2-[1-(3,4-Dichlorophenyl)-5-methyl-1H-1,2,4-triazol-3-ylsulfanyl]ethyl]piperidine oxalate | Flurazepam Related Compound C |
| 1-[2-Benzyloxy-1(R)-phenylethyl]-4-cyclohexylpiperazine dihydrochloride | Fluspirilene |
| 1-[3-(2-Oxo-3-phenylimidazolin-1-yl)propyl]spiro[piperidine-4,1'(3H)-isobenzofuran] hydrochloride; 1-Phenyl-3-[3-[spiro[piperidine-4,1'(3H)-isobenzofuran]-1-yl]propyl]imidazolin-2-one hydrochloride | GBR 12783 DiHCl |
| 1-[3-(3,4-Dimethoxyphenyl)propyl]-4-(4-phenylbutyl)perhydro-1,4-diazepine dihydrochloride | GBR 12909 DiHCl |
| 1-[3-(4-Chlorophenoxy)propyl]-4-methylpiperidine hydrochloride | GBR 13069 DiHCl |
| 1-[3-(4-Phenyl-2H-1,2,3-triazol-2-yl)propyl]piperidine | GBR-12935 DiHCl |
| 1-[4-(6-Methoxynaphthalen-1-yl)butyl]-3,3-dimethylpiperidine hydrochloride | GR 89696 Fumarate |
| 1-[4-[2-[1-(3,4-Dichlorophenyl)-1H-pyrazol-3-yloxy]ethyl]piperazin-1-yl]ethanone oxalate | Guanabenz Acetate |
| 11-[5-(4-Fluorophenyl)-5-oxopentyl]-5,6,7,8,9,10-hexahydro-7,10-iminocyclohept[b]Indole | Guanadrel Sulfate |
| 1-Benzyl-3beta-[3-(cyclopropylmethoxy)propyl]-2alpha,3alpha,4beta-trimethylpiperidine | Halofantrine HCl |
| 1-Benzyl-3-methoxy-3',4'-dihydrospiro(piperidine-4,1'-thieno[3,2-c]pyrane) | HEAT HCl |
| 1'-Benzyl-3-methoxy-4-phenyl-3,4-dihydrospiro[furo[3,4-c]pyrazole-1,4'-piperidine] | Hexylcaine HCl |

TABLE 1-continued

| | |
|---|---|
| 1-Benzyl-4-(4-fluorophenoxymethyl)piperidine | Hycanthone |
| 1-Benzyl-4-[2-(4-fluorophenyl)-2-oxoethyl]piperidine maleate | Hydroxychloroquine Sulfate |
| 1-Benzyl-4-[3-phenyl-2(E)-propenyloxymethyl]piperidine hydrochloride | IBZM, S(−)- |
| 1-Benzyl-4-[4-(4-fluorophenyl)-3-cyclohexen-1-yl]piperazine dihydrochloride hemihydrate | ICI-199,441 HCl |
| 1'-Benzylspiro[1,2,3,4-tetrahydronaphthalene-1,4'-piperidine] | Ifenprodil Tartrate |
| 1'-Benzylspiro[indane-1,4'-piperidine] | Indatraline HCl |
| 1'-Butyl-3-Methoxy-4-phenyl-3,4-dihydrospiro[furo[3,4-c]pyrazole-1,4'-piperidine] | Iofetamine HCl |
| 1-Cyclohexyl-4-(3-phenoxypropyl)piperazine dihydrochloride | Isamoltane Hemifumarate |
| 1-Hydroxy-1'-(2-phenylethyl)spiro[1,2,3,4-tetrahydronaphthalene-2,4'-piperidine] hydrochloride | Isoxsuprine HCl |
| 1-Methyl-4-[2-(4-phenylpiperidin-1-yl)ethyl]-4,5,6,7-tetrahydro-1H-indazole oxalate | Ketotifen Fumarate Salt |
| 1-Phenyl-3-(1-propyl-1,2,5,6-tetrahydropyridin-3-yl)-1-propanone oxime oxalate | L-693,403 Maleate |
| 1-Phenyl-4-(pyrrolidin-1-ylmethyl)-1,4,6,7-tetrahydropyrano[4,3-c]pyrazole | L-741,626 |
| 2-(2-{[1-(3-Chloro-Benzyl)-Pyrrolidin-3-Yl]-Methyl-Carbamoyl}-2-Methyl-Propyl)-4,6-Dimethyl-Benzoic Acid | L-741,742 HCl |
| 2-(3,4-Dichlorophenyl)-N-methyl-N-[2-(1,2alpha,3alpha,4beta-tetramethylpiperidin-3beta-yl)ethyl]acetamide | L-745,870 TriHCl |
| 2-(Cyclohexylmethylaminomethyl)-8-methoxy-3,4-dihydro-2H-1-benzopyran hydrochloride | Levetimide HCl, R(−) |
| 2(S)-[(3aS,6aR)-5-Butyl-4-oxo-1,2,3,3a,4,6a-hexahydrocyclopenta[c]pyrrol-2-yl]propionic acid ethyl ester | Levobunolol HCl |
| 2-[2-[5-Methyl-1-(2-naphthyl)-1H-pyrazol-3-yloxy]ethylamino]ethanol hydrochloride | Lidoflazine |
| 2-[2-(N-(Cyclobutylmethyl)-N-methylamino]ethyl]-1,2,3,4-tetrahydronaphthalen-2-one | Lobeline HCl |
| 2-[3-[4-(2-Methoxyphenyl)piperazin-1-yl]propoxy]-9H-carbazole | lomerizine diHCl |
| 2-[4-(4-Methoxybenzyl)piperazin-1-ylmethyl]-4H-1-benzopyran-4-one | Loxapine Succinate |
| 2-[N-[2-(3,4-Dichlorophenyl)ethyl]-N-methylaminomethyl]-1-ethylpyrrolidine | LY-53,857 Maleate |
| 2-Benzyl-3,4,8-trimethyl-2-azabicyclo[2.2.2]octane-6-carboxylic acid ethyl ester | Maprotiline HCl |
| 2-Butyl-2,3,4,4a,9,9a-hexahydro-1H-indeno[2,1-c]pyridine | Mazindol |
| 2-Chloro-11-(4-Methylpiperazino)Dibenz[B,F]Oxepin Maleate | MDL 12,330A HCl |
| 3-(1-Benzyl-2r,3c,4t-trimethylpiperidin-3t-yl)propionic acid ethyl ester hydrochloride | Mebhydroline 1,5-naphthalendisulfonate Salt |
| 3-(3-Chloro-4-cyclohexylphenyl)-1-(hexahydroazepin-1-yl)-1(Z)-propene hydrochloride; 1-[3-(3-Chloro-4-cyclohexylphenyl)-2(Z)-propenyl]hexahydroazepine hydrochloride | Meclizine HCl |
| 3-(4-Methylphenyl)-5-(1-propyl-1,2,5,6-tetrahydropyridin-3-yl)isoxazole oxalate | Mefloquine HCl |
| 3-(N-Benzyl-N-methylamino)-1-(4-nitrophenyl)piperidine | Meprylcaine HCl |
| 3,3'-Diethylthiacarbocyanine Iodide | Mesoridazine Besylate |
| 3-[1-(Benzocyclobutan-1-ylmethyl)piperidin-4-yl]-6-fluoro-1,2-benzisoxazole | Metaphit Methanesulfonate |
| 3-[2-(2-Adamantyl)ethyl]-3-azabicyclo[3.2.2]nonane | Metaphit |
| 3-[3-(4-Methylphenyl)isoxazol-5-yl]-1-propyl-1,2,5,6-tetrahydropyridine | Methantheline Bromide |
| 3a,6-Epoxy-2-[2-(4-fluorophenyl)ethyl]-2,3,3a,6,7,7a-hexahydro-1H-isoindole | Methdilazine |
| 3a,6-Epoxy-2-[2-(4-fluorophenyl)ethyl]perhydroisoindole | Methiothepin Mesylate |
| 3-Mercapto-2-Methylpropanoic Acid 1,2-Diphenylethylamine Salt | Methixene HCl |

TABLE 1-continued

| | |
|---|---|
| 3-Phenyl-1-(1-propyl-1,2,5,6-tetrahydro-3-pyridyl)-1-propanone oxime monohydrochloride | Methylene Violet 3Rax HCl |
| 3-Quinuclidinyl Benzilate | Metipranolol |
| 3-Tropanyl-3,5-Dichlorobenzoate | Mianserin HCl |
| 3-Tropanyl-Indole-3-Carboxylate HCl | Miconazole |
| 4-(1H-Indol-4-Yl)-Piperazine-1-Carboxylic Acid 2-(5-Bromo-2-Ethoxy-Phenylamino)-Cyclohexylmethyl Ester | ML-9 HCl |
| 4-(2-Tert-Butylsulfanyl-Benzyl)-Piperazine-1-Carboxylic Acid 2-Thiophen-2-Yl-Ethyl Ester | Morantel Hydrogen L-Tartrate |
| 4-(3,5-Dimethoxy-Phenyl)-Piperazine-1-Carboxylic Acid 1-(2-Fluoro-Benzyl)-Piperidin-2-Ylmethyl Ester | MR 16728 HCl |
| 4-(3-Nitro-5-Sulfamoyl-Thiophen-2-Yl)-Piperazine-1-Carboxylic Acid 1-(2-Fluoro-5-Methoxy-Benzyl)-Piperidin-3-Ylmethyl Ester | MT-210 |
| 4-(4-Benzylpiperazin-1-ylmethyl)-7-methoxy-2H-1-benzopyran-2-one | N-(2-Adamantyl)-N-[2-(2-adamantyl)ethyl]-N-methylamine hydrochloride |
| 4-(4-Bromophenyl)-5-[2-(dihexylamino)ethyl]thiazol-2-amine dihydrochloride | N-[1-(2-Indanyl)piperidin-4-yl]-N-methylcarbamic acid isobutyl ester fumarate |
| 4-(4-Fluorobenzoyl)-1-(4-Phenylbutyl)Piperidine Oxalate | N-[1-[4-Methoxy-3-(2-phenylethoxy)benzyl]-4-methylpentyl]-N-propylamine |
| 4-(4-Methylphenyl)-1-(3-morpholinopropyl)-1,2,3,6-tetrahydropyridine | N-[2-(3,4-Dichlorophenyl)ethyl]-N-ethyl-N-[2-(1-pyrrolidinyl)ethyl]amine |
| 4-(5-Trifluoromethyl-Pyridin-2-Yl)-Piperazine-1-Carboxylic Acid Pent-2-Ynyl Ester | N-[2-(3,4-Dichlorophenyl)ethyl]-N-methyl-N-(2-pyrrolidinoethyl)amine dihydrobromide |
| 4-(Dimethylamino)-1-phenylcyclohexanol | N-[4-[4-(Diethylamino)piperidin-1-yl]phenyl]methanesulfonamide |
| 4,7-Epoxy-2-[2-(4-fluorophenyl)ethyl]-2,3,3a,4,7,7a-hexahydro-1H-isoindole | N1-(1-Adamantyl)-N2-(2-methylphenyl)acetamidine |
| 4-[1-(3-[18F]fluoropropyl)piperidin-4-ylmethoxy]benzonitrile | N1-[2-(3,4-Dichlorophenyl)ethyl]-N1,N2,N2-trimethyl-1,2-ethanediamine |
| 4-[1-(4-Chlorobenzyl)-4-(benzylpiperidin-4-yl]-2-hydroxy-4-oxobut-2-enoic acid | Nafronyl Oxalate Salt |
| 4-[1-(4-Fluorophenyl)-1-hydroxymethyl]-1-[3-(4-fluorophenoxy)propyl]piperidine | Naftifine |
| 4-[2-(Dipropylamino)ethyl]-2-(2-phenylethoxy)anisole hydrochloride | Naftopidil diHCl |
| 4-[2-(Dipropylamino)ethyl]-5,8-dimethylcarbazole hydrochloride | Naltriben Mesylate |
| 4-[2-[1-(3,4-Dichlorophenyl)-5-methyl-1H-pyrazol-3-yloxy]ethyl]morpholine | NE-100 |
| 4-[2-[1-(Cyclopropylmethyl)piperidin-4-yl]acetyl]benzonitrile fumarate | Nefazodone |
| 4-[4-(N-Benzyl-N-methylamino)piperidin-1-yl]benzonitrile | N-Ethyl-N-[2-(1-piperidinyl)ethyl]-N-[2-[4-(trifluoromethoxy)phenyl]ethyl]amine |
| 4-[N-[2-[N'-(4-Fluorobenzyl)-N'-methylamino]ethyl]-N-methylamino]-1-(4-fluorophenyl)-1-butanone dihydrochloride | Nicergoline |
| 4-Benzyl-1-[4-(4-fluorophenyl)-4-hydroxybutyl]piperidine hydrochloride | Niguldipine HCl, (+/−)- |
| 4-Bromo-N-[1-(9-Ethyl-9H-Carbazol-3-Ylmethyl)-Pyrrolidin-3-Yl]-2-Trifluoromethoxy-Benzenesulfonamide | Nisoxetine HCl |
| 4'-Chloro-3-Alpha-(Diphenylmethoxy)Tropane HCl | NP-07 |
| 4-Furan-2-Ylmethyl-Piperazine-1-Carboxylic Acid 2-{4-[3-(2-Trifluoromethyl-Phenothiazin-10-Yl)-Propyl]-Piperazin-1-Yl}-Ethyl Ester | Nylidrin HCl |
| 4-Methoxy-1-[2-(4-phenylpiperazin-1-yl)ethyl]-6H-dibenzo[b,d]pyran hydrochloride | Octoclothepin Maleate, (±)- |
| 4-Methoxy-N-[1-(7-Methoxy-Benzo[1,3]Dioxol-5-Ylmethyl)-Pyrrolidin-3-Yl]-Benzenesulfonamide | Oxamniquine |
| 4-Phenyl-1-(3-phenylpropyl)-4-(pyrrolidin-1-ylcarbonyl)piperidine | Oxamniquine Related Compound A |
| 5-(2-Pyrrolidinoethyl)-4-(2,4,6-trimethoxyphenyl)thiazole-2-amine dihydrochloride | Oxamniquine Related Compound B |
| 5-(N-Ethyl-N-Isopropyl)-Amiloride | Oxatomide |
| 6-[1-Hydroxy-2-[4-(2-phenylethyl)piperidin-1-yl]ethyl]-1,2,3,4-tetrahydroquinolin-2-one | Oxiconazole Nitrate |
| 6-[2-(4-Benzylpiperidin-1-yl)ethyl]-3-methylbenzothiazol-2(3H)-one | Panamesine hydrochloride |
| 6-[2-4-(2-Phenylethyl)piperidin-1-yl]ethyl]-1,2,3,4-tetrahydroquinolin-2-one | Panaxatriol |
| 6-[3-(Morpholin-4-yl)propyl]benzothiazol-2(3H)-one | PAPP |

TABLE 1-continued

| | |
|---|---|
| 6-[6-(4-Hydroxypiperidin-1-yl)hexyloxy]-3-methyl-2-phenyl-4H-1-benzopyran-4-one | Paroxetine |
| 7-(4-Methoxyphenyl)-4-[4-(4-pyridyl)butyl]hexahydro-1,4-thiazepine | Paxilline |
| 7-[3-[4-(4-Fluorobenzoyl)piperidin-1-yl]propoxy]-4H-1-benzopyran-4-one hydrochloride | p-Chlorobenzhydrylpiperazine |
| 9-[4-({[4'-(trifluoromethyl)-1,1'-biphenyl-2-yl]carbonyl}amino)piperidin-1-yl]-N-(2,2,2-trifluoroethyl)-9H-fluorene-9-carboxamide | Penbutolol Sulfate |
| 9-Hydroxy-2,3,6,7,7a,8,12b,12c-octahydro-1H,5H-naphtho[1,2,3-ij]quinolizine | Pentamidine Isethionate |
| Acetophenazine Maleate | Pergolide Methanesulfonate |
| Acrinol | Perospirone |
| Ajmaline | Phenamil Methanesulfonate |
| Alaproclate HCl | Phenosafranin HCl |
| Aloe-Emodin | Piboserod |
| Alprenolol D-Tartrate Salt Hydrate | Pimozide |
| Alprenolol HCl | Pinacyanol Chloride |
| AMI-193 | Pindobind, (+/−)- |
| Aminobenztropine | Piperacetazine |
| Amiodarone HCl | Piperidolate HCl |
| Amodiaquine HCl | Pirenperone |
| Amorolfine HCl | PPHT HCl, (±)- |
| Amoxapine | Prenylamine Lactate Salt |
| AN2/AVex-73; AE-37; ANAVEX 2-73; N-(2,2-Diphenyltetrahydrofuran-3-ylmethyl)-N,N-dimethylamine | Pridinol Methanesulfonate Salt |
| Anavex 1-41; AE-14; N-(5,5-Diphenyltetrahydrofuran-3-ylmethyl)-N,N-dimethylamine hydrochloride | Procyclidine HCl |
| Anavex 19-144; AE-37met; AN19/AVex-144 | Proflavine Hemisulfate Salt |
| Anavex 7-1037 | Propafenone HCl |
| Anisotropine Methylbromide | Proparacaine HCl |
| Anpirtoline | Propiomazine |
| ARC 239 DiHCl | Protokylol |
| Auramine O HCl | Protriptyline HCl |
| Azaperone | Pyrilamine Maleate |
| Azatadine Maleate | Pyrimethamine |
| Azelastine HCl | Pyrrolidine-1,2-Dicarboxylic Acid 1-[1-(4-Allyloxy-Benzyl)-Piperidin-2-Ylmethyl] Ester 2-Benzyl Ester |
| Bamethan sulfate | Pyrvinium Pamoate |
| BD 1008 DiHBr | Quetiapine Fumarate |
| BD-1063 | Quinacrine HCl |
| Benextramine TetraHCl | Quinaldine Red |
| Benfluorex HCl | Quipazine Dimaleate |
| Benidipine HCl | Quipazine, 6-Nitro-, Maleate |
| Benoxathian HCl | Raloxifene |
| Benproperine Phosphate | Rimantadine HCl |
| Benzododecinium bromide | Rimcazole hydrochloride |
| Benzphetamine HCl | Risperidone |
| Benztropine Mesylate | Ritanserin |
| Bephenium Hydroxynaphthoate | Ritodrine HCl |
| Bepridil HCl | RS 23597-190 HCl |
| Berberine chloride | RS 67333 HCl |
| Betaxolol HCl | RS 67506 HCl |
| Bifemelane | Safranin O HCl |
| BMY 7378 DiHCl | Salmeterol |
| Bopindolol Malonate | SB203186 |
| BP 554 Maleate | SCH-23390 HCl, R(+)- |
| Bromhexine HCl | Sertaconazole Nitrate |
| Bromodiphenhydramine HCl | Sertindole |
| Bromperidol | Sertraline |
| Brompheniramine Maleate | Sibutramine HCl |
| BTCP HCl | Siramesine hydrochloride |
| Buclizine HCl | SKF-525A HCl |
| Buflomedil HCl | SKF-96365 HCl |
| Bupropion HCl | SNC 121 |
| Buspirone HCl | Spiperone HCl |
| Butacaine Sulfate | T-226296 |
| Butaclamol HCl, (±)- | Tegaserod Maleate |
| Butenafine HCl | Terbinafine HCl |
| Butoconazole Nitrate | Terconazole |
| BW 723C86 HCl | Terfenadine |
| Carbetapentane Citrate | Terfenadine Related Compound A |
| Carbinoxamine Maleate | Tetrindole Mesylate |
| Carpipramine DiHCl DiH2O | Thiethylperazine Malate |
| Carvedilol | Thioperamide Maleate |
| Cephapirin Benzathine | Thioproperazine |

TABLE 1-continued

| | |
|---|---|
| CGS-12066A Maleate | Thioridazine |
| Chloroprocaine HCl | Thiothixene |
| Chlorpheniramine Maleate | Thiothixene, (E)- |
| Chlorphenoxamine HCl | Thonzonium Bromide |
| Chlorprothixene | Tioconazole Related Compound A |
| Cinanserin HCl | TMB-8 HCl |
| Cinnarizine | Tolterodine L-Tartrate |
| Cirazoline HCl | Toremifene Citrate |
| Cis-(+/−)-N-Methyl-N-[2-(3,4-Dichlorophenyl)Ethyl]-2-(1-Pyrrolidinyl)Cyclohexamine DiHBr | Tramazoline HCl |
| Cis(Z)-Flupentixol DiHCl | Trans-U-50488 Methanesulfonate, (±)- |
| cis-2-(Cyclopropylmethyl)-7-(4-fluorobenzoyl)perhydropyrido[1,2-a]pyrazine | Tridihexethyl Chloride |
| cis-2-[4-(Trifluoromethyl)benzyl]-3a,4,7,7a-tetrahydroisoindoline | Trifluoperazine HCl |
| Cisapride Hydrate | Trifluperidol HCl |
| Citalopram HBr | Trihexyphenidyl HCl |
| Clemastine Fumarate | Trimeprazine Hemi-L-Tartrate |
| Clemizole HCl | Trimipramine Maleate |
| Clenbuteral HCl | Tripelennamine HCl |
| Clidinium Bromide | Triprolidine HCl |
| Clobenpropit 2HBr | Triprolidine HCl Z Isomer |
| Clofazimine | Tropanyl 3,5-Dimethylbenzoate |
| Clofilium Tosylate | Tropine 2-(4-Chlorophenoxy)Butanoate, Maleate |
| Clomiphene Citrate | U-50488 HCl, (−)- |
| Clomiphene Related Compound A | U-62066 |
| Clomipramine | UH 232 Maleate, (+)- |
| Cloperastine HCl | Vesamicol HCl |
| Clorgyline HCl | Vinpocetine |
| Clozapine | W-7 HCl |
| Conessine | WB-4101 HCl |

Preferably, the table above also includes reduced haloperidol. Reduced haloperidol is an active metabolite of haloperidol that is produced in humans, shows a high affinity (in the low nanomolar range) for sigma-1 receptors, and produces an irreversible blockade of sigma-1 receptors both in experimental animals and human cells.

Examples of well known methods of producing a prodrug of a given acting compound are known to those skilled in the art (e.g. in Krogsgaard-Larsen et al., Textbook of Drug Design and Discovery, Taylor & Francis (April 2002)).

Preferably the sigma ligand in the context of the present invention has the general formula (I) as depicted above.

In a preferred embodiment, $R_1$ in compounds of formula (I) is selected from H, —$COR_8$, and substituted or unsubstituted alkyl. More preferably, $R_1$ is selected from H, methyl and acetyl. A more preferred embodiment is when $R_1$ is H.

In another preferred embodiment, $R_2$ represents H or alkyl, more preferably methyl.

In yet another preferred embodiment of the invention, $R_3$ and $R_4$ are situated in the meta and para positions of the phenyl group, and preferably, they are selected independently from halogen and substituted or unsubstituted alkyl.

In an especially preferred embodiment of the invention, both $R_3$ and $R_4$ together with the phenyl group form an optionally substituted fused ring system (for example, a substituted or unsubstituted aryl group or a substituted or unsubstituted, aromatic or non-aromatic heterocyclyl group may be fused), more preferably, a naphthyl ring system.

Also, embodiments where n is selected from 2, 3, 4 are preferred in the context of the present invention, more preferably n is 2.

Finally, in another embodiment it is preferred that $R_5$ and $R_6$ are, each independently, $C_{1-6}$alkyl, or together with the nitrogen atom to which they are attached form a substituted or unsubstituted heterocyclyl group a, in particular a group chosen among morpholinyl, piperidinyl, and pyrrolidinyl group. More preferably, $R_5$ and $R_6$ together form a morpholine-4-yl group.

In additional preferred embodiments, the preferences described above for the different substituents are combined. The present invention is also directed to such combinations of preferred substitutions in the formula (I) above. In preferred variants of the invention, the combination of the invention encompasses a sigma ligand of formula (I) selected from:

[1] 4-{2-(1-(3,4-dichlorophenyl)-5-methyl-1H pyrazol-3-yloxy)ethyl}morpholine

[2] 2-[1-(3,4-Dichlorophenyl)-5-methyl-1H-pyrazol-3-yloxy]-N,N-diethylethanamine

[3] 1-(3,4-Dichlorophenyl)-5-methyl-3-[2-(pyrrolidin-1-yl)ethoxy]-1H-pyrazole

[4] 1-(3,4-Dichlorophenyl)-5-methyl-3-[3-(pyrrolidin-1-yl)propoxy]-1H-pyrazole

[5] 1-{2-[1-(3,4-Dichlorophenyl)-5-methyl-1H-pyrazol-3-yloxy]ethyl}piperidine

[6] 1-{2-[1-(3,4-dichlorophenyl)-5-methyl-1H-pyrazol-3-yloxy]ethyl}-1H-imidazole

[7] 3-{1-[2-(1-(3,4-Dichlorophenyl)-5-methyl-1H-pyrazol-3-yloxy)ethyl]piperidin-4-yl}-3H-imidazo[4,5-b]pyridine

[8] 1-{2-[1-(3,4-Dichlorophenyl)-5-methyl-1H-pyrazol-3-yloxy]ethyl}-4-methylpiperazine

[9] Ethyl 4-{2-[1-(3,4-dichlorophenyl)-5-methyl-1H-pyrazol-3-yloxy]ethyl}piperazine carboxylate

[10] 1-(4-(2-(1-(3,4-dichlorophenyl)-5-methyl-1H-pyrazol-3-yloxy)ethyl)piperazin-1-yl)ethanone

[11] 4-{2-[1-(4-Methoxyphenyl)-5-methyl-1H-pyrazol-3-yloxy]ethyl}morpholine

[12] 1-(4-Methoxyphenyl)-5-methyl-3-[2-(pyrrolidin-1-yl)ethoxy]-1H-pyrazole

[13] 1-(4-Methoxyphenyl)-5-methyl-3-[3-(pyrrolidin-1-yl)propoxy]-1H-pyrazole

[14] 1-[2-(1-(4-Methoxyphenyl)-5-methyl-1H-pyrazol-3-yloxy)ethyl]piperidine
[15] 1-{2-[1-(4-Methoxyphenyl)-5-methyl-1H-pyrazol-3-yloxy]ethyl}-1H-imidazole
[16] 4-{2-[1-(3,4-Dichlorophenyl)-5-phenyl-1H-pyrazol-3-yloxy]ethyl}morpholine
[17] 1-(3,4-Dichlorophenyl)-5-phenyl-3-[2-(pyrrolidin-1-yl)ethoxy]-1H-pyrazole
[18] 1-(3,4-Dichlorophenyl)-5-phenyl-3-[3-(pyrrolidin-1-yl)propoxy]-1H-pyrazole
[19] 1-{2-[1-(3,4-Dichlorophenyl)-5-phenyl-1H-pyrazol-3-yloxy]ethyl}piperidine
[20] 1-{2-[1-(3,4-Dichlorophenyl)-5-phenyl-1H-pyrazol-3-yloxy]ethyl}-1H-imidazole
[21] 2-{2-[1-(3,4-dichlorophenyl)-5-phenyl-1H-pyrazol-3-yloxy]ethyl}-1,2,3,4-tetrahydroisoquinoline
[22] 4-{4-[1-(3,4-Dichlorophenyl)-5-methyl-1H-pyrazol-3-yloxy]butyl}morpholine
[23] 1-(3,4-Dichlorophenyl)-5-methyl-3-[4-(pyrrolidin-1-yl)butoxy]-1H-pyrazole
[24] 1-{4-[1-(3,4-Dichlorophenyl)-5-methyl-1H-pyrazol-3-yloxy]butyl}piperidine
[25] 1-{4-[1-(3,4-Dichlorophenyl)-5-methyl-1H-pyrazol-3-yloxy]butyl}-4-methylpiperazine
[26] 1-{4-[1-(3,4-Dichlorophenyl)-5-methyl-1H-pyrazol-3-yloxy]butyl}-1H-imidazole
[27] 4-[1-(3,4-Dichlorophenyl)-5-methyl-1H-pyrazol-3-yloxy]-N,N-diethylbutan-1-amine
[28] 1-{4-[1-(3,4-dichlorophenyl)-5-methyl-1H-pyrazol-3-yloxy]butyl}-4-phenylpiperidine
[29] 1-{4-[1-(3,4-dichlorophenyl)-5-methyl-1H-pyrazol-3-yloxy]butyl}-6,7-dihydro-1H-indol-4(5H)-one
[30] 2-{4-[1-(3,4-dichlorophenyl)-5-methyl-1H-pyrazol-3-yloxy]butyl}-1,2,3,4-tetrahydroisoquinoline
[31] 4-{2-[1-(3,4-dichlorophenyl)-5-isopropyl-1H-pyrazol-3-yloxy]ethyl}morpholine
[32] 2-[1-(3,4-Dichlorophenyl)-5-isopropyl-1H-pyrazol-3-yloxy]-N,N-diethylethanamine
[33] 1-(3,4-Dichlorophenyl)-5-isopropyl-3-[2-(pyrrolidin-1-yl)ethoxy]-1H-pyrazole
[34] 1-(3,4-Dichlorophenyl)-5-isopropyl-3-[3-(pyrrolidin-1-yl)propoxy]-1H-pyrazole
[35] 1-{2-[1-(3,4-Dichlorophenyl)-5-isopropyl-1H-pyrazol-3-yloxy]ethyl}piperidine
[36] 2-{2-[1-(3,4-Dichlorophenyl)-5-isopropyl-1H-pyrazol-3-yloxy]ethyl}-1,2,3,4-tetrahydroisoquinoline
[37] 4-{2-[1-(3,4-dichlorophenyl)-1H-pyrazol-3-yloxy]ethyl}morpholine
[38] 2-[1-(3,4-dichlorophenyl)-1H-pyrazol-3-yloxy]N,N-diethylethanamine
[39] 1-(3,4-dichlorophenyl)-3-[2-(pyrrolidin-1-yl)ethoxy]-1H-pyrazole
[40] 1-{2-[1-(3,4-dichlorophenyl)-1H-pyrazol-3-yloxy]ethyl}piperidine
[41] 1-(3,4-dichlorophenyl)-3-[3-(pyrrolidin-1-yl)propoxy]-1H-pyrazole
[42] 1-{2-[1-(3,4-Dichlorophenyl)-5-methyl-1H-pyrazol-3-yloxy]ethyl}piperazine
[43] 1-{2-[1-(3,4-Dichlorophenyl)-5-methyl-1H-pyrazol-3-yloxy]ethyl}pyrrolidin-3-amine
[44] 4-{2-[1-(3,4-Dichlorophenyl)-4,5-dimethyl-1H-pyrazol-3-yloxy]ethyl}morpholine
[45] 4-{2-[1-(3,4-Dichlorophenyl)-4,5-dimethyl-1H-pyrazol-3-yloxy]ethyl}morpholine
[46] 2-[1-(3,4-Dichlorophenyl)-4,5-dimethyl-1H-pyrazol-3-yloxy]-N,N-diethylethanamine
[47] 1-(3,4-Dichlorophenyl)-4,5-dimethyl-3-[2-(pyrrolidin-1-yl)ethoxy]-1H-pyrazole
[48] 1-(3,4-Dichlorophenyl)-4,5-dimethyl-3-[3-(pyrrolidin-1-yl)propoxy]-1H-pyrazole
[49] 1-{2-[1-(3,4-Dichlorophenyl)-4,5-dimethyl-1H-pyrazol-3-yloxy]ethyl}piperidine
[50] 4-{4-[1-(3,4-dichlorophenyl)-1H-pyrazol-3-yloxy]butyl}morpholine
[51] (2S,6R)-4-{4-[1-(3,4-dichlorophenyl)-1H-pyrazol-3-yloxy]butyl}-2,6-dimethylmorpholine
[52] 1-{4-[1-(3,4-Dichlorophenyl)-1H-pyrazol-3-yloxy]butyl}piperidine
[53] 1-(3,4-Dichlorophenyl)-3-[4-(pyrrolidin-1-yl)butoxy]-1H-pyrazole
[55] 4-[1-(3,4-dichlorophenyl)-1H-pyrazol-3-yloxy]-N,N-diethylbutan-1-amine
[56] N-benzyl-4-[1-(3,4-dichlorophenyl)-1H-pyrazol-3-yloxy]-N-methylbutan-1-amine
[57] 4-[1-(3,4-dichlorophenyl)-1H-pyrazol-3-yloxy]-N-(2-methoxyethyl)-N-methylbutan-1-amine
[58] 4-{4-[1-(3,4-dichlorophenyl)-1H-pyrazol-3-yloxy]butyl}thiomorpholine
[59] 1-[1-(3,4-Dichlorophenyl)-5-methyl-3-(2-morpholinoethoxy)-1H-pyrazol-4-yl]ethanone
[60] 1-{1-(3,4-dichlorophenyl)-5-methyl-3-[2-(pyrrolidin-1-yl)ethoxy]-1H-pyrazol-4-yl}ethanone
[61] 1-{1-(3,4-dichlorophenyl)-5-methyl-3-[2-(piperidin-1-yl)ethoxy]-1H-pyrazol-4-yl}ethanone
[62] 1-{1-(3,4-dichlorophenyl)-3-[2-(diethylamino)ethoxy]-5-methyl-1H-pyrazol-4-yl}ethanone
[63] 4-{2-[5-Methyl-1-(naphthalen-2-yl)-1H-pyrazol-3-yloxy]ethyl}morpholine
[64] N,N-Diethyl-2-[5-methyl-1-(naphthalen-2-yl)-1H-pyrazol-3-yloxy]ethanamine
[65] 1-{2-[5-Methyl-1-(naphthalen-2-yl)-1H-pyrazol-3-yloxy]ethyl}piperidine
[66] 5-Methyl-1-(naphthalen-2-yl)-3-[2-(pyrrolidin-1-yl)ethoxy]-1H-pyrazole or their pharmaceutically acceptable salts, isomers, prodrugs or solvates.

In a more preferred variant of the invention, the sigma ligand of formula (I) is 4-{2-[5-Methyl-1-(naphthalen-2-yl)-1H-pyrazol-3-yloxy]ethyl} morpholine. This particular compound is designated in the examples of the present invention as compound 63.

The compounds of formula (I) and their salts or solvates can be prepared as disclosed in the previous application WO2006/021462.

As defined previously, "chemotherapeutic drugs" in the sense of this invention are compounds used in chemotherapy, especially those that impair mitosis (cell division) by targeting fast-dividing cells effectively. As these drugs cause damage to cells, they are termed cytotoxic. Some drugs cause cells to undergo apoptosis (so-called "cell suicide").

In a preferred embodiment of the invention, the chemotherapeutic drug is selected from drugs derived from platin, especially the platin-derivatives cisplatin, carboplatin and oxaliplatin; plant alkaloids and terpenes (terpenoids).

"Plant alkaloids" (and terpenoids) are alkaloids derived from plants that block cell division by preventing microtubule function. Since microtubules are vital for cell division, their inhibition also arrests cell mitosis. The main examples of plant alkaloids are vinca alkaloids and taxanes.

"Vinca alkaloids" bind to specific sites on tubulin, inhibiting the assembly of tubulin into microtubules (M phase of the cell cycle). They are derived from the Madagascar periwinkle, *Catharanthus roseus* (formerly known as *Vinca rosea*). The vinca alkaloids include Vincristine, Vinblastine, Vinorelbine, and Vindesine.

"Taxanes" are derived from the Pacific yew tree, *Taxus brevifolia*. Taxanes enhance the stability of microtubules, preventing the separation of chromosomes during anaphase. Preferred taxanes in this invention include Paclitaxel and Docetaxel.

Examples of chemotherapeutic drugs (by their trademarks) that can induce emesis that can be prevented or treated with sigma ligands are:

13-cis-Retinoic Acid, 2-CdA, 2-Chlorodeoxyadenosine, 5-fluorouracil 5-FU, 6-Mercaptopurine, 6-MP, 6-TG 6-Thioguanine, Abraxane, Accutane®, Actinomycin-D, Adriamycin®, Adrucil®, Agrylin®, Ala-Cort®, Aldesleukin, Alemtuzumab, ALIMTA, Alitretinoin, Alkaban-AQ®, Alkeran®, All-transretinoic acid, Alpha interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic trioxide, Asparaginase, ATRA, Avastin®, Azacitidine, BCG, BCNU, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine wafer, Casodex®, CC-5013, CCNU (o), CDDP (t), CeeNU (t), Cerubidine (t), cetuximab, Chlorambucil, Cisplatin, Citrovorum Factor, Cladribine, Cortisone, Cosmegen (t), CPT-11 (o), Cyclophosphamide, Cytadren (t), Cytarabine, Cytarabine liposomal, Cytosar-U (t), Cytoxan®, Dacarbazine, Dactinomycin, Darbepoetin alfa, Daunomycin, Daunorubicin, Daunorubicin hydrochloride (t), Daunorubicin liposomal, DaunoXome (t), Decadron, Delta-Cortef (t), Deltasone (t), Denileukin, diftitox, DepoCyt (t), Dexamethasone, Dexamethasone acetate, dexamethasone sodium phosphate, Dexasone (t), Dexrazoxane, DHAD (o), DIC (t), Diodex (t), Docetaxel, Doxil (t), Doxorubicin, Doxorubicin liposomal, Droxia (t), DTIC, DTIC-Dome (t), Duralone (t), Efudex (t), Eligard (t), Ellence (t), Eloxatin (t), Elspar (t), Emcyt (t), Epirubicin, Epoetin alfa, Erbitux, Erlotinib, Erwinia L-asparaginase (t), Estramustine, Ethyol, Etopophos (t), Etoposide, Etoposide phosphate (t), Eulexin (t), Evista (t), Exemestane, Fareston (t), Faslodex (t), Femara®, Filgrastim, Floxuridine, Fludara (t), Fludarabine, Fluoroplex (t), Fluorouracil, Fluorouracil (cream), Fluoxymesterone, Flutamide, Folinic Acid (o), FUDR (t), Fulvestrant, G-CSF (t), Gefitinib, Gemcitabine, Gemtuzumab ozogamicin, Gemzar (t), Gleevec™, Gliadel wafer (t), GM-CSF (o), Goserelin, granulocyte—colony stimulating factor (t), Granulocyte macrophage colony stimulating factor (O), Halotestin (t), Herceptin (t), Hexadrol (t), Hexalen (t), Hexamethylmelamine (t), HMM (t), Hycamtin (t), Hydrea (t), Hydrocort Acetate (t), Hydrocortisone, Hydrocortisone sodium phosphate. Hydrocortisone sodium succinate. Hydrocortone phosphate (t), Hydroxyurea, Ibritumomab, Ibritumomab Tiuxetan, Idamycin®, Idarubicin Ifex®, IFN-alpha, Ifosfamide, IL-11, IL-2, lmatinib mesylate, Imidazole Carboxamide, Interferon alfa, Interferon Alfa-2b (PEG conjugate) (o), Interleukin-2 (t), Interleukin-11 (o), Intron A® (interferon alfa-2b), Iressa®, Innotecan, Isotretinoin, Kidrolase (t), Lanacort (t), L-asparaginase (t), LCR (o), Lenalidomide (Lenolidamide), Letrozole, Leucovorin, Leukeran (t), Leukine (t), Leuprolide, Leurocristine (o), Leustatin (t), Liposomal Ara-C (t), Liquid Pred (t), Lomustine, L-PAM (o), L-Sarcolysin (o), Lupron (t), Lupron Depot (t), Matulane (t), Maxidex (t), Mechlorethamine, Mechlorethamine Hydrochloride, Medralone (t), Medrol®, Megace (t), Megestrol, Megestrol Acetate (o), Melphalan, Mercaptopurine, Mesna, Mesnex (t), Methotrexate, Methotrexate Sodium (o), Methylprednisolone, Meticorten (t), Mitomycin, Mitomycin-C (o), Mitoxantrone, M-Prednisol (t), MTC (o), MTX (o), Mustargen (t), Mustine, Mutamycin (t), Myleran (t), Mylocel (t), Mylotarg (t), Navelbine (t), Nelarabine, Neosar (t), Neulasta (t), Neumega (t), Neupogen (t), Nexavar®, Nilandron (t), Nilutamide, Nipent®, Nitrogen Mustard (o), Novaldex (t), Novantrone (t), Octreotide, Octreotide acetate (o), Oncospar (t), Oncovin (t), Ontak (t), Onxal (t), Oprevelkin, Orapred (t), Orasone (t), Oxaliplatin, Paclitaxel, Paclitaxel Protein-bound, Pamidronate, Panretin (t), Paraplatin (t), Pediapred (t), PEG Interferon, Pegaspargase, Pegfilgrastim, PEG-INTRON (t), PEG-L-asparaginase, Pemetrexed, Pentostatin, Phenylalanine Mustard (o), Platinol (t), Platinol-AQ (t), Prednisolone, Prednisone, Prelone (t), Procarbazine, PROCRIT®, Proleukin (t), Prolifeprospan 20 with Carmustine implant (t), Purinethol (t), Raloxifene, Revlimid®, Rheumatrex (t), Rituxan (t), Rituximab, Roferon-A®, (interferon alfa-2a) Rubex (t), Rubidomycin hydrochloride (t), Sandostatin®, Sandostatin LAR (t), Sargramostim, Solu-Cortef (t), Solu-Medrol (t), Sorafenib, STI-571, Streptozocin, SU11248, Sunitinib, Sutent®, Tamoxifen, Tarceva®, Targretin (t), Taxol®, Taxotere (t), Temodar®, Temozolomide, Teniposide, TESPA (o), Thalidomide, Thalomid®, TheraCys (t), Thioguanine, Thioguanine Tabloid (t), Thiophosphoamide (o), Thioplex (t), Thiotepa, TICE®, Toposar (t), Topotecan, Toremifene, Tositumomab, Trastuzumab, Tretinoin, Trexall (t), Trisenox (t), TSPA (o), VCR (o), Velban (t), Velcade®, VePesid (t), Vesanoid (t), Viadur (t), Vidaza (t), Vinblastine, Vinblastine Sulfate (o), Vincasar Pfs (t), Vincristine, Vinorelbine, Vinorelbine tartrate (o), VLB (o), VM-26 (o), VP-16 (t), Vumon (t), Xeloda®, Xyotax, Zanosar (t), Zevalin™, Zinecard (t), Zoladex®, Zoledronic acid, and Zometa O.

Another drugs used in cancer-therapy (mostly as chemotherapeutics) are:

(as trademarks): Aldara, Alimta, Androcur, Arimidex, Borea, Caelyx, Campto, Casodex, Decapeptyl, Eloxatin, Eutirox, Faslodex, Femara, Gemzar, Gonapeptyl, Grisetin, Herceptin, Isovorin, Lysodren, Megefren, Metvix, Navelbine, Novaldex, Novantrone, Paraplatin, Procrin, Prostacur, Suprefact, Tamoxifeno Funk, Taxol, Taxotere, Testex, Elmu/Prolongatum, Tomudex, Utefos, Vepesid, Xeloda, Zoladex;

(as active compounds): Anastrozole, Bicalutamide, Busereline, Capecetabine, Cisplatin, Carboplatin, Desoxorubicin, Docetaxel, Etoposid, Fulvestrant, Gemcitabine, Gosereline, Irinotecan, Letrozole, Leuproreline, Megestrol, Mitotane, Mitoxantrone, Oxaliplatin, Paclitaxel, Pemetrexed, Raltitrexed, Tamoxiphen, Tegafur, Triptoreline, Vincristine, Vinblastine, Vinorelbine, and Vindesine.

In a preferred embodiment of the invention, the chemotherapeutic drug is selected from taxanes, vinca alkaloids and drugs derived from platinum. Preferably, the chemotherapeutic drug is selected from paclitaxel, oxaliplatin and vincristine.

In a more preferred embodiment of the invention, the chemotherapeutic drug is Paclitaxel. Paclitaxel (Taxol®) is one of the most effective and commonly used antineoplasic drugs for the treatment of solid tumours.

In another more preferred embodiment of the invention, the chemotherapeutic drug is Oxaliplatin.

In another more preferred embodiment of the invention, the chemotherapeutic drug is Vincristine.

Preferred combinations of the invention comprise the combination of 4-{2-[5-Methyl-1-(naphthalen-2-yl)-1H- pyrazol-3-yloxy]ethyl}morpholine (compound 63) with a chemotherapeutic drug selected from Paclitaxel, Oxaliplatin and Vincristine.

More preferred combinations of the invention comprise the combination of 4-{2-[5-Methyl-1-(naphthalen-2-yl)-1H-pyrazol-3-yloxy]ethyl}morpholine with Paclitaxel and the combination of 4-{2-[5-Methyl-1-(naphthalen-2-yl)-1H-pyrazol-3-yloxy]ethyl}morpholine with Oxaliplatin.

The combination of the invention may be formulated for its simultaneous, separate or sequential administration, with at least a pharmaceutically acceptable carrier, additive, adjuvant or vehicle. This has the implication that the combination of the two active compounds may be administered:

- as a combination that is being part of the same medicament formulation, the two active compounds being then administered always simultaneously.
- as a combination of two units, each with one of the active substances giving rise to the possibility of simultaneous, sequential or separate administration.

In a particular embodiment, the sigma ligand is independently administered from the chemotherapeutic drug (i.e in two units) but at the same time.

In another particular embodiment, the sigma ligand is administered first, and then the chemotherapeutic drug is separately or sequentially administered.

These particular ways of administration are preferably used to prevent the emesis developing as a consequence of chemotherapy.

In yet another particular embodiment, the chemotherapeutic drug is administered first, and then the sigma ligand is administered, separately or sequentially, as defined.

This particular way of administration is preferably used to treat the emesis developing as a consequence of chemotherapy.

The auxiliary materials or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical combination in accordance with the invention can be adapted to any form of administration, be it orally or parenterally, for example pulmonar, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

Suitable preparations for oral applications are tablets, pills, chewing gums, capsules, granules, drops or syrups.

Suitable preparations for parenteral applications are solutions, suspensions, reconstitutable dry preparations or sprays.

The combination of the invention may be formulated as deposits in dissolved form or in patches, for percutaneous application.

Skin applications include ointments, gels, creams, lotions, suspensions or emulsions.

Suitable form of rectal application is by means of suppositories.

As mentioned above, the combination of at least one sigma ligand (such as a compound of general formula (I)) and at least one chemotherapeutic drug is suited for its use in the treatment of cancer and simultaneous prevention and/or treatment of emesis induced by chemotherapy. This combination could be administered simultaneously, separately or sequentially. Nevertheless, as chemotherapy is usually combined with radiotherapy, the combination is also useful for the treatment of cancer and simultaneous prevention and/or treatment of emesis resulting from radiotherapy.

In a particular embodiment, the sigma ligand according to the present invention is used in the prevention of emesis induced by chemotherapy or radiotherapy. In another particular embodiment, the sigma ligand according to the present invention is used in the treatment of emesis induced by chemotherapy or radiotherapy.

In a particular embodiment, the sigma ligand according to the present invention is used in the prevention of acute emesis induced by chemotherapy or radiotherapy. In another particular embodiment, the sigma ligand according to the present invention is used in the treatment of acute emesis induced by chemotherapy or radiotherapy.

In a particular embodiment, the sigma ligand according to the present invention is used in the prevention of delayed emesis induced by chemotherapy or radiotherapy. In another particular embodiment, the sigma ligand according to the present invention is used in the treatment of delayed emesis induced by chemotherapy or radiotherapy.

In a particular embodiment, the combination according to the present invention is used in the treatment of cancer and simultaneous prevention of emesis induced by chemotherapy or radiotherapy. In another particular embodiment, the combination according to the present invention is used in the treatment of cancer and simultaneous treatment of emesis induced by chemotherapy or radiotherapy.

As note previously, in a particular embodiment, sigma ligands (such as compounds of general formula (I)) are useful at the same time against the two main concerns relating to chemotherapy and radiotherapy: pain and emesis induced. Hence, a combination according to the present invention comprising at least a sigma ligand (such as a compound of general formula (I)) and at least one chemotherapeutic drug for simultaneous, separate or sequential administration, may be indicated for the treatment of cancer and simultaneous prevention and/or treatment of emesis and pain induced by chemotherapy or radiotherapy.

In one embodiment of the invention it is preferred that the sigma ligand is used in therapeutically effective amounts. The physician will determine the dosage of the present therapeutic agents which will be most suitable and it will vary with the form of administration and the particular compound chosen, and furthermore, it will vary with the patient under treatment, the age of the patient, the type of cancer and emesis being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

For example, the dosage regime that must be administered to the patient will depend on the patient's weight, the type of application, the condition and severity of the disease. A preferred dosage regime of comprises an administration of a compound of formula (I) within a range of 0.5 to 100 mg/kg and of the chemotherapeutic drug from 0.15 to 15 mg/kg and it is administered daily in one or several doses.

The following examples and figures are merely illustrative of certain embodiments of the invention and cannot be considered as restricting it in any way.

EXAMPLES

Example 1

Synthesis of 4-{2-[5-Methyl-1-(naphthalen-2-yl)-1H-pyrazol-3-yloxy]ethyl}morpholine (Compound 63) and its Hydrochloride Salt

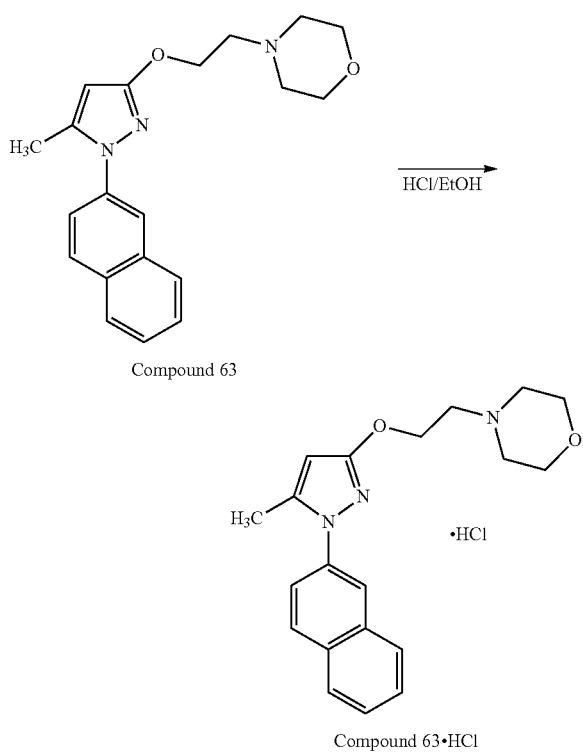

Compound 63 can be can be prepared as disclosed in the previous application WO2006/021462. Its hydrochloride can be obtained according the following procedure:

Compound 63 (6.39 g) was dissolved in ethanol saturated with HCl, the mixture was stirred then for some minutes and evaporated to dryness. The residue was crystallized from isopropanol. The mother liquors from the first crystallization afforded a second crystallization by concentrating. Both crystallizations taken together yielded 5.24 g (63%) of the corresponding hydrochloride salt (m.p.=197-199° C.)

$^1$H-NMR (DMSO-d$_6$) δ ppm: 10.85 (bs, 1H), 7.95 (m, 4H), 7.7 (dd, J=2.2, 8.8 Hz, 1H), 7.55 (m, 2H), 5.9 (s, 1H), 4.55 (m, 2H), 3.95 (m, 2H), 3.75 (m, 2H), 3.55-3.4 (m, 4H), 3.2 (m, 2H), 2.35 (s, 3H).

HPLC purity: 99.8%.

Example 2

Assessment of the Antimimetic Properties of Compound 63

The antiemetic properties of compound 63 were assessed in combination with intraperitoneal administration of the chemotherapeutic agent cisplatin in the conscious, unrestrained ferret (*Mustela putorius* furo). FIG. 1 shows these results.

Chemotherapeutic agents including cisplatin elicit an immediate emetic response on the day of therapy, that is, acute emesis, and also protracted nausea and vomiting lasting up to 5 days thereafter, that is, delayed emesis. Cisplatin damages the gastrointestinal epithelium and triggers acute emesis through stimulation of 5-HT3 receptors in abdominal afferent fibers, whereas the precise mechanism of delayed emesis has not been fully revealed. In the prevention of acute emesis, 5-HT3-receptor antagonists are effective in both animals and humans. In contrast, the incidence of delayed emesis is not sufficiently reduced by 5-HT3-receptor antagonists. Recent studies have suggested the involvement of substance P and NK1 receptors in the generation of delayed emesis following the treatment with chemotherapeutic agents 2.1 Procedures At least 12 days before their first treatment, ferrets were surgically implanted with telemetry devices. Individual body weights were recorded before treatment, at the time of telemetry device implantation, one day before the initiation of treatment and after completion of the treatment session, at the time of euthanasia, for each animal respectively.

The animals were treated according to the following schedule:

| Group | Description | Animal number | Dose level (mg/kg) | Dose volume (mL/kg) | Dose concentration (mg/mL) | Administration per day | Number of days of treatment |
|---|---|---|---|---|---|---|---|
| A | Vehicle (0.9% NaCl) | 1 to 4 | 0 | 2 | 0 | 3 | 3 |
| B | High dose | 5 to 8 | 80 | 2 | 40 | 1 | 1 |
| C | Low dose | 9 to 12 | 40 | 2 | 20 | 3 | 3 |
| D | High dose | 13 to 16 | 80 | 2 | 40 | 3 | 3 |

Group A, B, C and D animals were administered by the intraperitoneal route.

Animals were dosed and monitored as follows:

| Day no. | Group | Animal numbers |
|---|---|---|
| 0 to 3 | A, B, C and D | 1 and 2; 5 and 6; 9 and 10; 13 and 14 |
| 7 to 10 | A, B, C and D | 3 and 4; 7 and 8; 11 and 12; 15 and 16 |

In all groups (including group A), on days 0 and 7, cisplatin was administered at the dose level of 5 mg/kg intraperitoneally (5 mL/kg) on fasted animals.

In all groups, on days 0 and 7, the first treatment with the vehicle or the test item was administered 1 hour prior to cisplatin treatment.

Moreover, in group B, only one administration of test item was done (1 hour before cisplatin) whereas in groups A, C, and D, eight additional administrations were performed every 8 hours for 3 days.

Body temperature, abdominal pressure and activity of the abdominal muscle (EMG) were recorded in treated animals, on day 0 and day 7, respectively, starting approximately 1 hour before the first administration of the vehicle and the test item and for at least 72 hours following the first administration of the vehicle and the test item.

After the last scheduled measurement, animals were euthanized without necropsy.

2.2 Test System

Species/strain: Domestic ferret (*Mustela putorius* furo), descented and neutered.
Supplier: Marshall Bioresources, 5800 Lake Bluff Road, North Rose, N.Y. 14516 USA.
Number of animals in the study: 20 males.
Age at initiation of test: At least 19 weeks.
Body weight range at initiation of treatment (day 0 or 7): 1.0 to 1.5 kg.
Justification: the ferret is considered as the gold standard species for emesis screening.

2.3 Animal Husbandry

Housing: One room for the acclimatization period and another room for the test period (dosing and emesis observation), in an air-conditioned building (Building G7):
Temperature: 19 to 25° C.,
Relative humidity: ≥35%,
Air changes: Minimum 10 air changes per hour,
Lighting cycle: 12 hours light (artificial)/12 hours dark.
Environmental Conditions (Within Target Ranges Through The Test)
The normal dark cycle was interrupted (for up to 1 hour) to allow the +16 h, +40 h and +64 h treatments and the other scheduled procedures. These differences were considered not to have affected the health of the animals or the outcome of the study.
Caging: Animals were housed in 4 plastic cages (1100× 730×650 mm each). Each cage was connected by tubes to the other cages allowing the animals to exert their natural burrowing activity during the pretest period.
From the night before the first treatment onwards, animals were housed singly in plastic cage (900× 520×520 mm).
Bedding: Dust free and irradiated wood shaving (LAB SHAVING) made from coniferous tree wood. From 3 Aug. 2009 (day 6), the bedding was sterilised instead of being irradiated.
Diet: Ferret complete diet (Diet F, Dietex).
Quantity distributed: approximately 100 g diet/animal/ day.
Diet was distributed twice per day (approximately 50 g at each distribution) during pretest.
From the evening of the day before the first treatment, diet was distributed once per day (approximately 100 g). On days −1 and 6, treated animals received 150 g of diet (50 g the morning then 100 g at the end of the day).

Animals were fasted for approximately 1 hour before the first administration of the vehicle, the test item and the positive control on day 0 or day 7.
After telemetry device implantation, all animals received twice daily and during 3 days, 10 mL of a liquid food supplement (Fortol® C+, Intervet SA).
Water: Softened and filtered (0.2 μm) mains drinking water was available ad libitum (via bowls). Water is analysed twice a year for chemical and bacterial contaminants by Laboratoire Santé Environnement Hygiène de Lyon, France.

2.4 Pre-Treatment Procedures

Animal health procedure: By supplier, all animals received a standard vaccination (rabies and distemper) and were descented and castrated (surgeries on 12, 20 and 22 May 2003 and 24 Jun. 2009).
All animals received a clinical inspection for ill-health on arrival. During the acclimatisation period, animals were observed daily for clinical signs, and at least twice daily (at the beginning and at the end of the normal working day) for mortality/morbidity.
Acclimatisation period: At least 20 days between animal arrival and the start of treatment.
Body weight: Animals were weighed on arrival (data are maintained in the raw data of the study), on the day of implantation, on the day before allocation during the acclimatisation period, on the day before treatment and on the day of euthanasia.
Animal identification: Animals were identified by microchip implants (Electronic Laboratory Animal Monitoring System, Bio Medic Data Systems), inserted in the inter-scapular region by supplier on 04 or 30 Jun. 2009.
Allocation to treatment groups: Performed at random.

2.5 Animal Preparation

Telemetry Implantation Procedures:
At least 12 days before their first treatment, all animals were implanted with a telemetry device.
Surgical Procedures
24 hours before surgical procedures, animals received antibiotherapy with long acting amoxycilline (Clamoxyl® LA, Pfizer Italia SRL, 10 mg/kg, intramuscular).
Animals were anaesthetised with an intramuscular injection of ketamine hydrochloride (Imalgène 500®, Mèdal SAS; 10 mg/kg) and xylazine hydrochloride (Rompun® 2%, kvp Kiel; 2 mg/kg). The hair on the abdomen was clipped. During surgery, the level of anaesthesia was maintained with gaseous anaesthetic (1 to 3% isoflurane in oxygen). The transmitter body was implanted under aseptic conditions into the abdominal cavity.
Electromyographic (EMG) activity of the abdominal muscle was monitored by implanting the 2 biopotential leads (leads that extend out of the device body and consist of a helix of medical grade stainless steel wire inserted into a silicone tubing) into the left rectus abdomis muscle.
The abdominal pressure developed during abdominal muscles contractions of retching and/or expulsions was measured with the pressure catheter (polyurethane tubing that extends out of the device body) positioned intraperitoneally.
Post-Surgical Procedures
Antibiotic prophylaxis with long-acting amoxycilline (Clamoxyl® LA, Pfizer Italia SRL, mg/kg, intramuscular), once approximately 24 hours after surgical procedures, Analgesic prophylaxis with tolfenamic acid (Tolfédine 4%®, Laboratoire Vétoquinol SA, 4 mg/kg; intramuscular), once just after implantation and once 48 hours later.

2.6 Administration of Compound 63 and Vehicle

Route: Intraperitoneal.

Method of administration: Bolus injection using a sterile syringe and needle introduced intraperitoneally into the pelvic area.

Frequency: Groups A, C and D: one administration every 8 hours during 3 days (day 0 to 3 and day 7 to 10); for a total of 9 administrations ("multiple dose regimen"), Group B: one administration on day 0 or 7 ("single dose").

Volume of administration: 2 mL/kg.

Individual dose volumes were calculated using the latest recorded body weight.

Rationale for the choice of the route of administration: the intraperitoneal route was selected as a route of administration allowing a good plasma exposure.

2.7 Administration of Emetogenic Item

Route: Intraperitoneal.

Method of administration: Bolus injection using a sterile syringe and needle introduced intraperitoneally into the pelvic area.

Frequency: One administration for each animal, on day 0 or 7, one hour after the first treatment with the test item Volume of administration: 5 mL/kg.

Individual dose volumes were calculated using the latest recorded body weight.

2.8 Data Evaluation 2.8.1 Characterization of Emesis from Telemetry Signals

Emesis is characterized by rhythmic abdominal contractions that are either associated with oral expulsion of solid or liquid material from the gastrointestinal tract, that is vomiting, or not associated with the passage of material, that is retching movements. The characteristic pattern of the abdominal pressure and of the electromyographic activity of the abdominal wall during the vomiting reflex was used to characterize the emetogenic properties of the test item and the emetic response (time-course).

When judged necessary to allow a better evaluation, raw EMG signals were filtered, rectified and integrated.

2.8.2 Emetic Episodes Evaluation

For emetic episodes evaluation, retching and expulsion events were considered together.

For each animal, the number of retchings and expulsions per 1-hour epoch after cisplatin administration were determined.

Cisplatin-induced emesis was divided in two distinct phases:
the acute phase from 0 to 16 hours after cisplatin administration,
the delayed phase from 18 to 72 hours after cisplatin administration.

For each animal, the total number of retchings and expulsions was determined for the acute and the delayed phases.

The results are expressed as arithmetic mean±standard error of the mean (s.e.m.).

For evaluation of the antiemetic properties of the test item compound 63, the cisplatin-induced emesis was divided in two distinct phases the acute phase from 0 to 16 hours and the delayed phase from 18 to 72 hours.

Results

With the administration of compound 63, 80 mg/kg, multiple dose regimen (9 treatments), the number of emetic events during the delayed phase was markedly decreased, with a maximum total number of 39 EE between 62 and 63 hours (FIG. 1).

The invention claimed is:

1. A method for treating a patient afflicted with or at risk of emesis induced by chemotherapy or by radiotherapy comprising administering to the patient a selective sigma-1 receptor ligand in an amount effective to treat the patient, wherein the patient has cancer and is undergoing chemotherapy or radiotherapy and wherein the selective sigma-1 receptor ligand is 4-{2-[5-methyl-1-(naphthalen-2-yl)-1H-pyrazol-3-yloxy]ethyl} morpholine or a pharmaceutically acceptable salt or solvate thereof.

2. The method of claim 1, for the simultaneous treatment of chemotherapy or radiotherapy-induced emesis, and pain.

3. The method of claim 1, wherein the selective sigma-1 receptor ligand is 4-{2-[5-methyl-1-(naphthalen-2-yl)-1H-pyrazol-3-yloxy]ethyl} morpholine hydrochloride.

4. A method for the treatment of cancer and simultaneous treatment of emesis induced by chemotherapy or radiotherapy in a patient, comprising administering to the patient a therapeutically effective amount of a combination of at least one selective sigma-1 receptor ligand and a least one chemotherapeutic drug simultaneously, separately or sequentially, wherein the selective sigma-1 receptor ligand is 4-{2[5-methyl-1-(naphthalen-2-yl)-1H-pyrazol-3-yloxy]ethyl} morpholine or a pharmaceutically acceptable salt or solvate thereof.

5. The method of claim 4, wherein the chemotherapeutic drug is selected from the group consisting of taxanes, vinca alkaloids and drugs derived from platinum.

6. The method of claim 4, wherein the chemotherapeutic drug is selected from the group consisting of paclitaxel, oxaliplatin and vincristine.

7. The method of claim 4, comprising administering to the patient 4-{2-[5-methyl-1-(naphthalen-2-yl)-1H-pyrazol-3-yloxy]ethyl} morpholine or a pharmaceutically acceptable salt or solvate thereof and paclitaxel.

8. The method of claim 4, comprising administering to the patient 4-{2-[5-Methyl-1-(naphthalen-2-yl)-1H-pyrazol-3-yloxy]ethyl} morpholine or a pharmaceutically acceptable salt or solvate thereof and oxaliplatin.

9. The method of claim 4, comprising administering to the patient 4-{2-[5-Methyl-1-(naphthalen-2-yl)-1H-pyrazol-3-yloxy]ethyl} morpholine or a pharmaceutically acceptable salt or solvate thereof and vincristine.

10. The method of claim 4, wherein the selective sigma-1 receptor ligand is 4-{2-[5-methyl-1-(naphthalen-2-yl)-1H-pyrazol-3-yloxy]ethyl} morpholine hydrochloride.

11. The method of claim 4, comprising administering to the patient 4-{2-[5-methyl-1-(naphthalen-2-yl)-1H-pyrazol-3-yloxy]ethyl} morpholine hydrochloride and paclitaxel.

12. The method of claim 4, comprising administering to the patient 4-{2-[5-methyl-1-(naphthalen-2-yl)-1H-pyrazol-3-yloxy]ethyl} morpholine hydrochloride and oxaliplatin.

13. The method of claim 4, comprising administering to the patient 4-{2-[5-methyl-1-(naphthalen-2-yl)-1H-pyrazol-3-yloxy]ethyl} morpholine hydrochloride and vincristine.

* * * * *